United States Patent
Fujiyama et al.

(10) Patent No.: US 10,309,896 B2
(45) Date of Patent: Jun. 4, 2019

(54) DEVICE FOR DETECTING PLANT STRESS AND METHOD FOR DETECTING PLANT STRESS

(71) Applicant: PANASONIC INTELLECTUAL PROPERTY MANAGEMENT CO., LTD., Osaka (JP)

(72) Inventors: Takeshi Fujiyama, Fukuoka (JP); Yuuji Terashima, Fukuoka (JP); Kazuhiro Yanagi, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/525,431

(22) PCT Filed: Mar. 2, 2016

(86) PCT No.: PCT/JP2016/001132
§ 371 (c)(1),
(2) Date: May 9, 2017

(87) PCT Pub. No.: WO2016/174803
PCT Pub. Date: Nov. 3, 2016

(65) Prior Publication Data
US 2018/0284016 A1    Oct. 4, 2018

(30) Foreign Application Priority Data
Apr. 30, 2015 (JP) ................... 2015-093641

(51) Int. Cl.
*G01N 21/00* (2006.01)
*G01N 21/359* (2014.01)
(Continued)

(52) U.S. Cl.
CPC ............ *G01N 21/359* (2013.01); *A01G 7/04* (2013.01); *A01G 7/045* (2013.01); *A01H 1/04* (2013.01);
(Continued)

(58) Field of Classification Search
None
See application file for complete search history.

(56) References Cited

U.S. PATENT DOCUMENTS 9,128,049 B2 * 9/2015 Groz .................. G01N 21/3151
2015/0286340 A1 * 10/2015 Send ...................... G01S 17/46
345/175

(Continued)

FOREIGN PATENT DOCUMENTS

JP    2001-272373    10/2001

OTHER PUBLICATIONS

Hyperspectral remote sensing of agriculture. Sahoo et al, Mar. 2015.*
(Continued)

*Primary Examiner* — Delomia L Gilliard
(74) *Attorney, Agent, or Firm* — Greenblum & Bernstein, P.L.C.

(57) ABSTRACT

There is provided a plant stress detection apparatus including a first light source that radiates a reference beam of a first wavelength that has a characteristic of tending not to be absorbed in water toward a plant by optical scanning, a second light source that radiates a measuring beam of a second wavelength that has a characteristic of tending to be absorbed in water toward the plant by optical scanning, and a detector that detects presence or absence of water or undulation of the plant based on reflection light of the reference beam that is reflected at an irradiation position of the plant that has a first irradiation area and reflection light (Continued)

of the measuring beam that is reflected at an irradiation position of the plant that has a second irradiation area that is different from the first irradiation area.

10 Claims, 21 Drawing Sheets

(51) Int. Cl.
*A01G 7/04* (2006.01)
*A01H 3/02* (2006.01)
*A01H 1/04* (2006.01)
*G01N 21/3554* (2014.01)
*G01N 21/31* (2006.01)

(52) U.S. Cl.
CPC ........... *A01H 3/02* (2013.01); *G01N 21/3554* (2013.01); *G01N 21/3151* (2013.01); *Y02P 60/146* (2015.11)

(56) References Cited

U.S. PATENT DOCUMENTS

2016/0054113 A1\* 2/2016 Osawa ............... G01B 9/02083
356/497
2017/0115210 A1  4/2017 Fujiyama et al.

OTHER PUBLICATIONS

International Search Report issued in International Patent Application No. PCT/JP2016/001132, dated Jun. 7, 2016.

\* cited by examiner

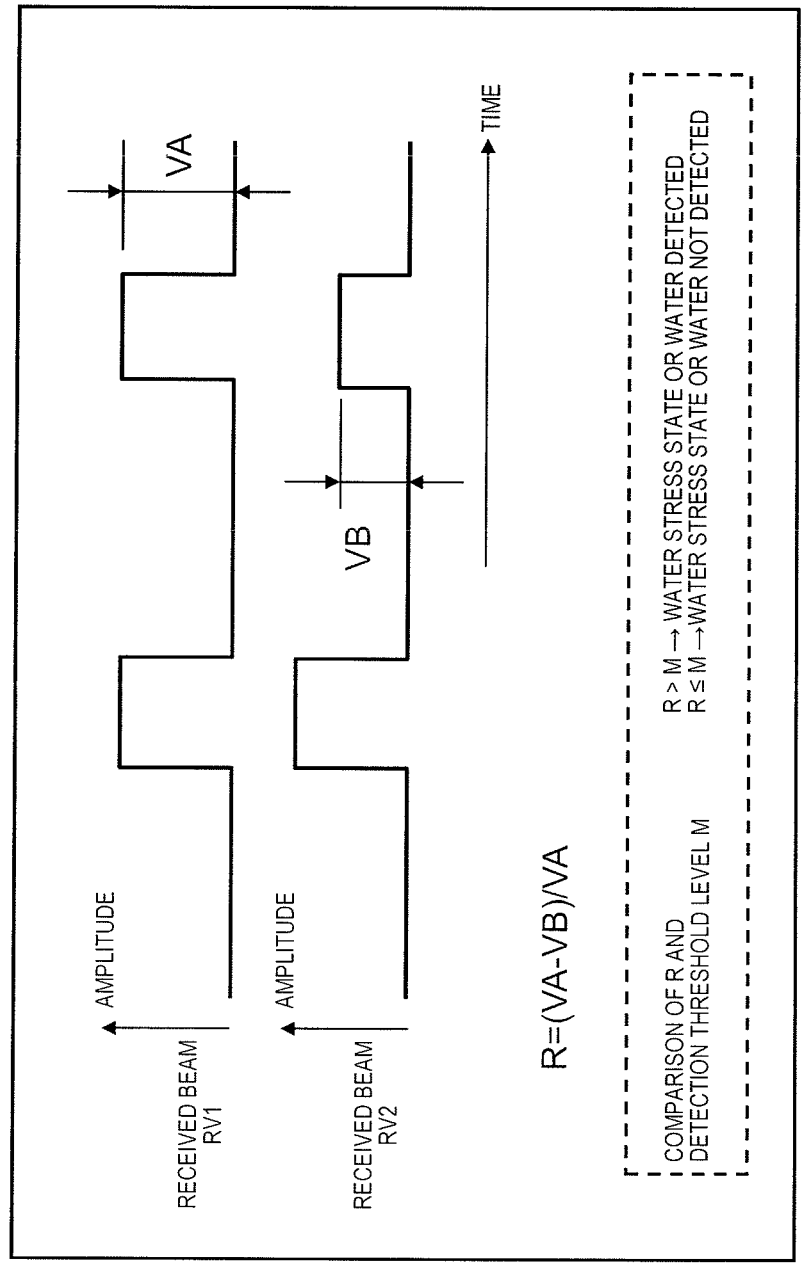

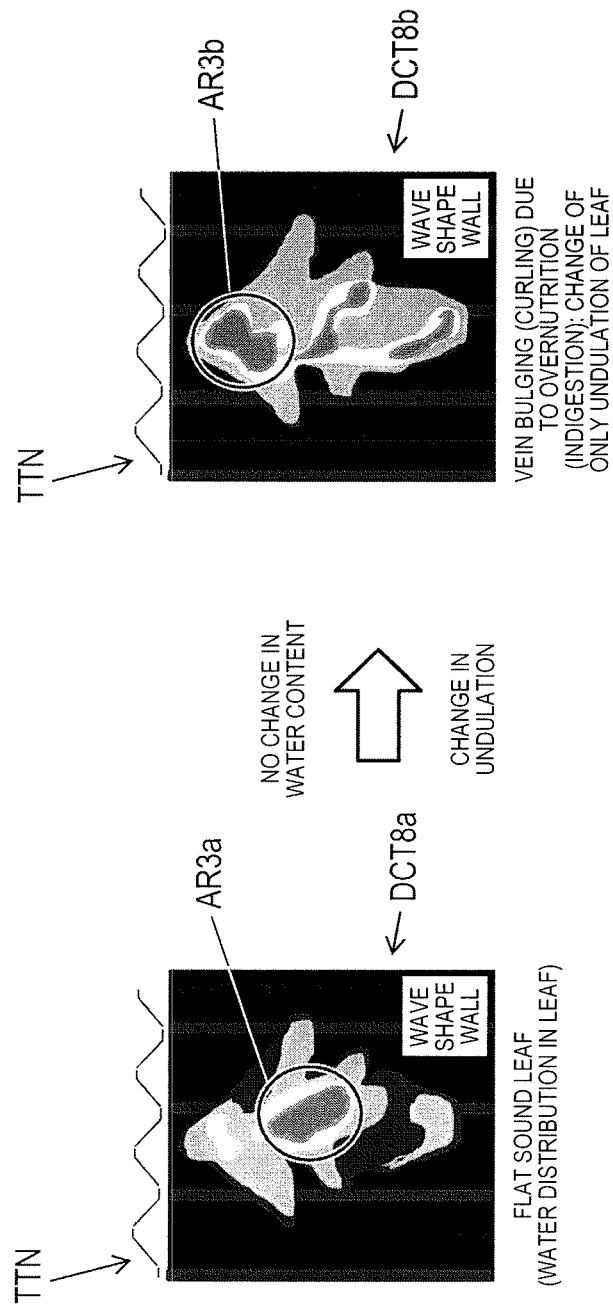

DEVICE FOR DETECTING PLANT STRESS AND METHOD FOR DETECTING PLANT STRESS

TECHNICAL FIELD

The present disclosure relates to a plant stress detection apparatus and a plant stress detection method which detects a distribution relating to presence or absence of stress obtained to plant.

BACKGROUND ART

There is a potential difference inside and outside of a cell in a normal plant and electromotive force is generated. It is possible to describe a mechanism which generates such electromotive force based on, for example, an electrophysiological model of an axial organ of a higher plant. In particular, various methods are suggested in which a state of a root of the plant (for example, water stress) is examined non-destructively utilizing electromotive force between the root and soil.

As a technique in which water stress in a plant is measured utilizing the method described above, for example, PTL 1 discloses connecting a first nonpolarizable electrode to the plant, connecting a second nonpolarizable electrode to soil in which the plant is planted, providing a potentiometer between the two nonpolarizable electrodes, and being able to measure water stress which is received by the plant by measuring electromotive force between both nonpolarizable electrodes using the potentiometer.

The present disclosure has an object of providing a plant stress detection apparatus and a plant stress detection method which precisely detect a distribution relating to at least presence or absence of at least water stress obtained to plant without making work of an observer complex.

CITATION LIST

Patent Literature

PTL 1: Japanese Patent Unexamined Publication No. 2001-272373

SUMMARY OF THE INVENTION

A plant stress detection apparatus of the present disclosure includes a first light source that radiates a reference beam of a first wavelength that has a characteristic of tending not to be absorbed in water toward a plant by optical scanning, a second light source that radiates a measuring beam of a second wavelength that has a characteristic of tending to be absorbed in water toward the plant by optical scanning, and a detector that detects presence or absence of water and undulation of the plant based on reflection light of the reference beam that is reflected at an irradiation position of the plant that has a first irradiation area and reflection light of the measuring beam that is reflected at an irradiation position of the plant that has a second irradiation area that is different from the first irradiation area.

A plant stress detection method of the present disclosure is a plant stress detection method in a plant stress detection apparatus, the method including radiating a reference beam of a first wavelength that has a characteristic of tending not to be absorbed in water toward a plant by optical scanning, radiating a measuring beam of a second wavelength that has a characteristic of tending to be absorbed in water toward the plant by optical scanning, and detecting presence or absence of water and undulation of the plant based on reflection light of the reference beam that is reflected at an irradiation position of the plant that has a first irradiation area and reflection light of the measuring beam that is reflected at an irradiation position of the plant that has a second irradiation area that is different from the first irradiation area.

According to the present disclosure, it is possible to detect with high precision a distribution state which relates to at least presence or absence of water stress of the plant without making work of an observer complex.

BRIEF DESCRIPTION OF DRAWINGS

FIG. 6 is a principle explanatory diagram of detection of water or undulation in an invisible light sensor;

FIG. 17A is a diagram illustrating an example of the transition of the distribution of undulation of the leaf of the plant in a case such that a water content is not changed, but fertilizer that is supplied to the plant is changed to increase;

DESCRIPTION OF EMBODIMENTS

An embodiment, which specifically exemplifies the plant stress detection apparatus and the plant stress detection method according to the present disclosure (hereinafter referred to as "embodiment") will be described in detail with reference to the accompanying drawings. However, detailed description may be omitted as necessary. For example, detailed description of already well-known matter and overlapping description with respect to substantially the same configuration may be omitted. This is because the following description is prevented from unnecessarily becoming redundant, and a process of the inventor is easily set. Drawings and the following description are provided by the inventor for sufficient understanding of the present disclosure, and thereby, the present disclosure is not intended to be limited to a subject described in the range of the claims.

Figure 1:
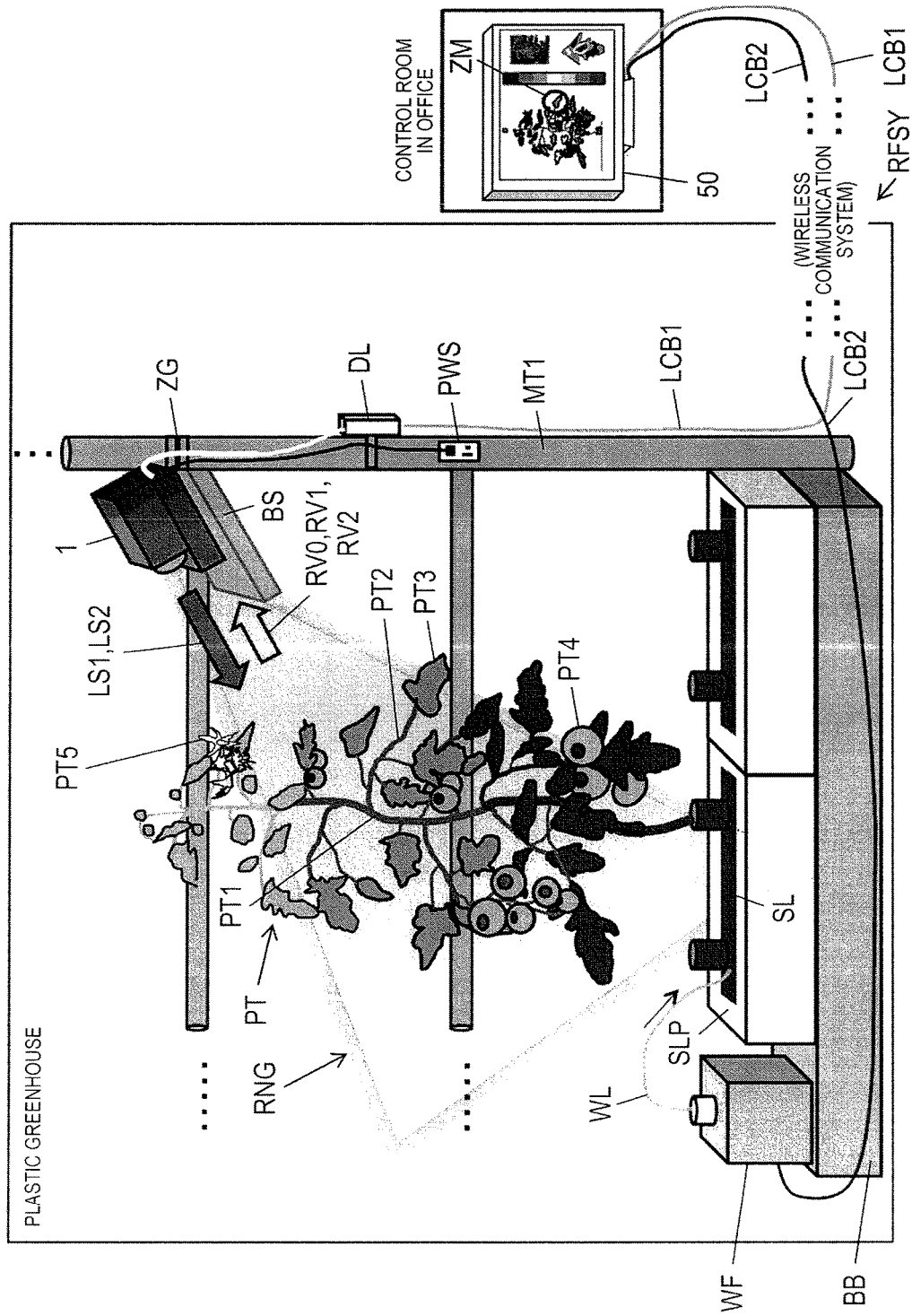
FIG. 1 is a conceptual explanatory diagram illustrating an example of usage circumstances of a plant stress detection camera in an embodiment.

Description is made exemplifying plant stress detection camera 1 indicated in FIG. 1 as an example of the plant stress detection apparatus of the present embodiment. The present embodiment is able to be expressed as the plant stress detection method which executes each process that is performed by the plant stress detection camera. However, the plant stress detection apparatus of the present embodiment is not limited to plant stress detection camera 1 illustrated in FIG. 1. Here, in PTL 1, description is made considering measurement of presence or absence of water stress of the plant, but for example, measurement of presence or absence of a shape (in detail, undulation) of the leaf of the plant is not considered. Plant stress detection camera 1 of the present embodiment is able to detect a distribution state of presence or absence of water of the plant and is also able to detect the distribution state of presence or absence of, for example, the shape (in detail, undulation) of the leaf of the plant.

In the description below, the state of undulation refers to a state in which it is possible to confirm that an observation target (for example, the leaf of the plant) has a shape in an oblique direction with respect to an optical axis direction of plant stress detection camera 1. Accordingly, a state in which it is possible to confirm that the observation target (for example, the leaf of the plant) has a shape in a vertical direction with respect to the optical axis direction of plant stress detection camera 1 is a state in which there is no undulation.

Here, the observation target of plant stress detection camera 1 of the present embodiment is the plant, and description is made by exemplifying a fruit vegetable that is given as a more specific example. Since sugar content of a fruit of a tomato is increased in growth of fruit vegetables such as, for example, the tomato, it is known that it is necessary for water or fertilizer to be in an insufficient state and not a state in which water or fertilizer is sufficiently supplied as a result of water or fertilizer of a root or a leaf being digested by a suitable amount in photosynthesis. For example, if sufficient water is supplied to the leaf, the leaf has a flat shape in a sound state. Meanwhile, when water of the leaf is equivalently insufficient, the shape of the leaf is bent. In addition, if the fertilizer is excessively supplied, undulation is generated in the shape of the leaf due to the veins bulging. Meanwhile, when fertilizer in the soil is equivalently insufficient, a condition is generated of the leaf turning yellow and the like. In the present embodiment below, an example is described in which plant stress detection camera 1 radiates laser beams of a plurality of types which are different in wavelength on the plant (for example leaf), and detects water and undulation of the leaf based on an intensity rate of respective diffuse reflection light that are reflected on irradiation positions of the leaf.

Outline of Plant Stress Detection Camera

FIG. 1 is a conceptual explanatory diagram illustrating an example of usage circumstances of plant stress detection camera 1 in the present embodiment. Plant stress detection camera 1 is installed at a fixed point within a plastic greenhouse in which, for example, fruit vegetables such as the tomato are planted. In detail, for example, plant stress detection camera 1 is installed on base BS that is fixed to mounting jig ZG which is attached so as to interpose support column MT1 with a cylindrical shape extend in a vertical direction from the ground. Plant stress detection camera 1 operates by a power source to be supplied from power source switch PWS that is attached to support column MT1, and radiates reference beam LS1 and measuring beam LS2 that are a plurality of types of laser beams which have different wavelengths toward plant PT that is the observation target across irradiation range RNG.

Plant PT is, for example, a fruit vegetable plant such as the tomato, a root of plant PT which grows from soil SL that is filled in soil pot SLP which is installed on base BB, and plant PT has each of stem PT1, stalk PT2, leaf PT3, fruit PT4, and flower PT5. Fertilizer water supply device WF is installed on base BB. Fertilizer water supply device WF supplies water to soil spot SLP via, for example, cable WL according to an instruction from wireless communication system RFSY that is connected via local area network (LAN) cable LCB2. Thereby, since water is supplied to soil SL, the root of plant PT absorbs water, and transmits water to each part within plant PT (that is, stem PT1, stalk PT2, leaf PT3, fruit PT4, and flower PT5).

In addition, plant stress detection camera 1 receives diffuse reflection light RV1 and RV2 that are reflected on an irradiation position of plant PT which is radiated by reference beam LS1 and measuring beam LS2, and furthermore, receives ambient light RV0. As will be described later, plant stress detection camera 1 has a normal camera function, and is able to image an image (that is, image of plant PT within the plastic greenhouse indicated in FIG. 1) within a default angle of view due to ambient light RV0 entering. Plant stress detection camera 1 outputs output data which includes various detection results (refer to description below) or image data to data logger DL based on diffuse reflection light RV1 and RV2.

Data logger DL transmits output data from plant stress detection camera 1 to management personal computer (PC, not illustrated) of a control room within an office at a position geographically separated from the plastic greenhouse via LAN cable LCB1 and wireless communication system RFSY. Wireless communication system RFSY is not particularly limited in communication specification, but controls communication between data logger DL within the plastic greenhouse and management PC within the control room in the office, and furthermore transmits an instruction from management PC which relates to supply of water or fertilizer of soil pot SLP to fertilizer water supply device WF.

Monitor 50 is connected to management PC within the control room in the office, and management PC displays output data of plant stress detection camera 1 that is transmitted from data logger DL on monitor 50. In FIG. 1, for example, monitor 50 displays the entirety of plant PT that is the monitoring target and a distribution state which relates to presence or absence of water in the entirety of plant PT. In addition, monitor 50 generates and is able to comparatively display an enlargement distribution state of a specific designated location out of the entirety of plant PT (that is, designated location ZM that is specified by a zoom operation of an observer who uses management PC) and image data corresponding to the designated location of the enlargement distribution state.

Plant stress detection camera 1 has a configuration which includes visible light camera VSC and invisible light sensor NVSS. Visible light camera VSC (acquiring unit) images plant PT within the plastic greenhouse using ambient light RV0 with respect to invisible light that has a predetermined wavelength (for example, 0.4 to 0.7 µm) in the same manner as, for example, existing monitoring camera. Image data of the plant that is imaged by visible light camera VSC refers to "visible light camera image data".

Invisible light sensor NVSS incidents reference beam LS1 and measuring beam LS2 which is invisible light (for example, infrared beam) that has a plurality of types of wavelengths (refer to description below) with respect to the same plant PT as visible light camera VSC. Invisible light sensor NVSS detects presence or absence of water and undulation at the irradiation position of plant PT which is the monitoring target using the intensity rate of diffuse reflection light RV1 and RV2 that are reflected on the irradiation position of plant PT which is radiated by reference beam LS1 and measuring beam LS2.

In addition, in visible light camera image data that is imaged by visible light camera VSC, plant stress detection camera 1 generates and outputs output image data (hereinafter referred to as "detection result image data") which is equivalent to the detection result of water or undulation of invisible light sensor NVSS or display data that composites information which relates to detection result image data. Display data is not limited to image data in which detection result image data and visible light camera image data are composited, and for example, may be image data that is generated such that detection result image data and visible light camera image data are able to be compared. An output destination of the display data from plant stress detection camera 1 is an externally connected device that is connected to plant stress detection camera 1 via, for example, a network (not illustrated), and is data logger DL or communication terminal MT (refer to FIG. 2). The network may be a wired network (for example, intranet or internet), and may be a wireless network (for example, wireless LAN).

Description of Each Part of Plant Stress Detection Camera

Figure 2:
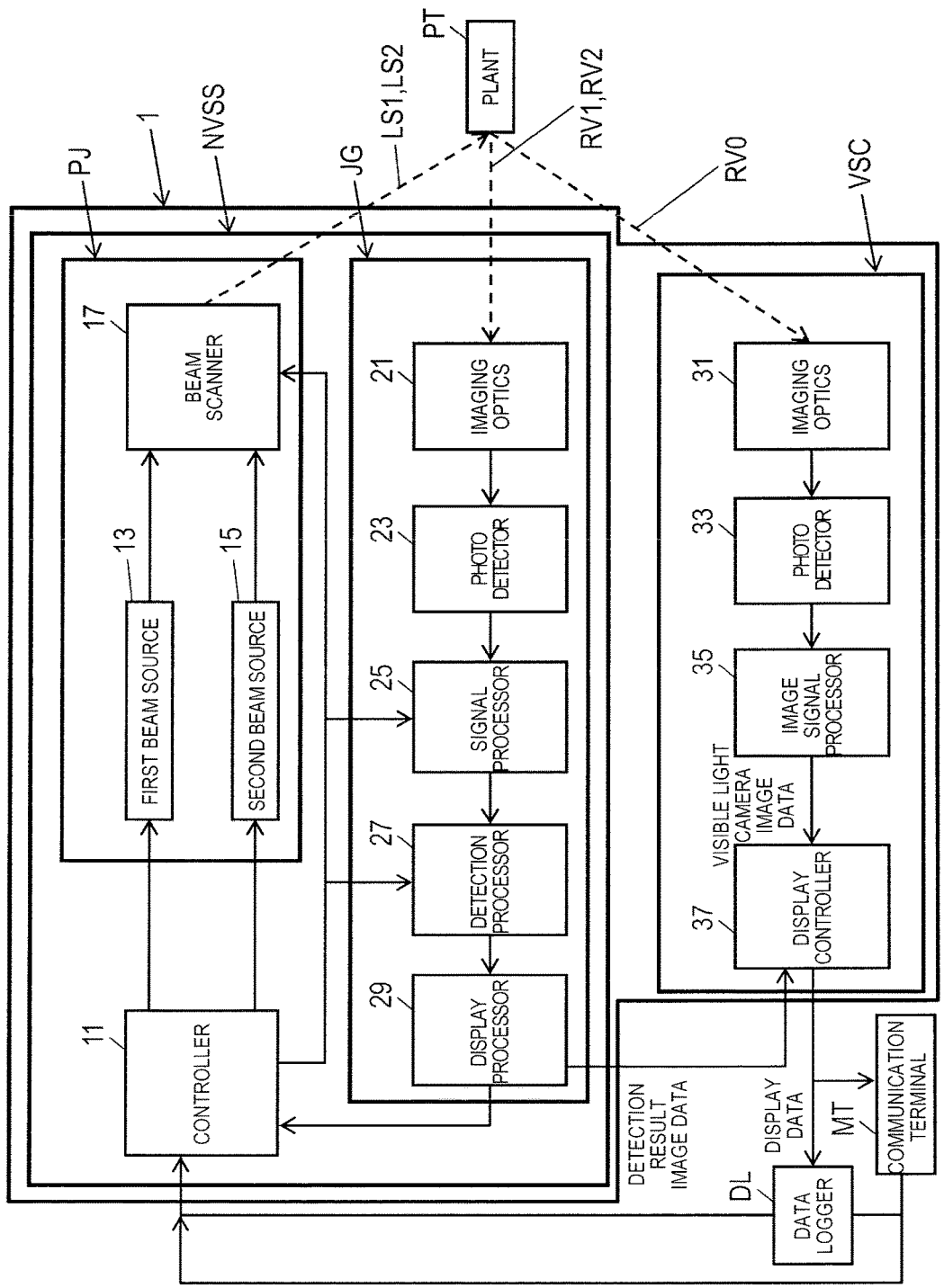
FIG. 2 is a block diagram illustrating in detail an example of an internal configuration of the plant stress detection camera in the embodiment.

FIG. 2 is a block diagram illustrating in detail an example of an internal configuration of plant stress detection camera 1 of the present embodiment. Plant stress detection camera 1 which is indicated in FIG. 2 has a configuration which includes invisible light sensor NVSS and visible light camera VSC. Invisible light sensor NVSS has a configuration which includes controller 11, beam output PJ, and determiner JG. Beam output PJ has first beam source 13, second beam source 15, and beam scanner 17. Determiner JG has imaging optics 21, photo detector 23, signal processor 25, detection processor 27, and detection processor 29. Visible light camera VSC has imaging optics 31, photo detector 33, image signal processor 35, and display controller 37. Communication terminal MT is portable by a user (for example, observer of growth of plant PT of fruit vegetable plant such as the tomato, hereinafter the same).

In the description of each part of plant stress detection camera 1, controller 11, invisible light sensor NVSS, and visible light camera VSC are described in order.

Controller 11 is configured using, for example, a central processor (CPU), a micro processor unit (MPU), or a digital signal processor (DSP), (and also configured using, for example, a program memory and a work memory,) and performs a signal process for totally controlling an operation control of each part of visible light camera VSC and invisible light sensor NVSS, an input and output process of data within other parts, a computing process of data, and a storage process of data. In addition, controller 11 includes timing controller 11a described later (refer to FIG. 3).

When controller 11 acquires information on a detection target distance that is sent due to an input operation of a user of data logger DL or communication terminal MT, a detection target distance range from plant stress detection camera 1 of a specific material (for example, plant PT) in which invisible light sensor NVSS is the detection target is calculated, and the acquired detection target distance or the calculated detection target distance range information is set to signal processor 25 or detection processor 27 described later. Controller 11 sets detection threshold level M of plant PT which is the detection target of invisible light sensor NVSS to detection processor 27 described later. Details of the operation of controller 11 will be described later with reference to FIG. 4.

Controller 11 includes a first motor (not illustrated) for controlling beam diameter of reference beam LS1 that is incident from first beam source 13 (in other words, irradiation area of reference beam LS1 in plant PT) and a second motor (not illustrated) for controlling a beam diameter of measuring beam LS2 that is incident from second beam source 15 (in other words, irradiation area of measuring beam LS2 in plant PT).

Timing controller 11a controls output timing of first beam source 13 and second beam source 15 in beam output PJ. In detail, timing controller 11a outputs timing signal for beam scanning TR to first beam source 13 and second beam source 15 in a case where light is incident to first beam source 13 and second beam source 15.

In addition, during the start of a predetermined incidence period, timing controller 11a alternately outputs beam output signal RF to first beam source 13 and second beam source 15. In detail, during the start of the incidence period of an odd number of times, timing controller 11a outputs beam output signal RF to first beam source 13 and during the start of the incidence period of an even number of times, outputs beam output signal RF to second beam source 15. Beam output signal RF is input to distance/water and undulation detector 27a of detection processor 27 as a signal (reference signal) that illustrates a start timing during measurement of distance from plant stress detection camera 1 to plant PT.

Next, each part of invisible light sensor NVSS is described.

When first beam source 13 as an example of the first light source receives timing signal for beam scanning TR from timing controller 11a of controller 11, reference beam LS1 (for example, near infrared beam) that is a laser beam of invisible light that has a predetermined wavelength (for example, 905 nm) is incident on plant PT via beam scanner 17 according to beam output signal RF from timing controller 11a in each incidence period (default value) of an odd number of times. In the present embodiment, reference beam LS1 that is incident from first beam source 13 is used in measurement of distance from plant stress detection camera 1 to the irradiation position of plant PT that is an object to be detected. Wavelength 905 nm of reference beam LS1 is a wavelength which has a characteristic of tending not to be absorbed in water (refer to FIG. 8).

Presence or absence of detection of water or undulation in plant PT may be determined by comparing to the predetermined detection threshold level M. Detection threshold level M may be a predetermined value, may be an arbitrarily set value, and furthermore, may be a value based on intensity of the diffuse reflection light that is acquired in a state in which there is no water or no undulation (for example, a value in which a predetermined margin is added to a value of intensity of the diffuse reflection light that is obtained in a state in which there is no water or no undulation). That is, presence or absence of detection of water or undulation may be determined by comparing detection result image data that is acquired in a state in which there is no water or no undulation and detection result image data that is acquired thereafter. In this manner, it is possible to set a threshold level appropriate for an environment in which plant stress detection camera 1 is installed as detecting threshold level M of presence or absence of water or undulation by acquiring intensity of the diffuse reflection light in the state in which there is no water or no undulation.

When second beam source 15 as an example of the second light source receives timing signal for beam scanning TR from timing controller 11a of controller 11, measuring beam LS2 (for example, infrared beam) that is the laser beam of invisible light that has a predetermined wavelength (for example, 1550 nm) is incident on plant PT via beam scanner 17 according to beam output signal RF from timing controller 111a in each incidence period (default value) of an even number of times. In the present embodiment, measuring beam LS2 that is incident from second beam source 15 is used in determination of presence or absence of detection of water or undulation in plant PT. Wavelength 1550 nm of measuring beam LS2 is a wavelength which has a characteristic in which light tends to be absorbed in water (refer to FIG. 8).

Thereby, plant stress detection camera 1 is able to measure the distance from plant stress detection camera 1 to the irradiation position of plant PT using an irradiation time of reference beam LS1 and a light receiving time of diffuse reflection light RV1 at the irradiation position of the plant PT that is irradiated with reference beam LS. Furthermore, plant stress detection camera 1 detects presence or absence of water or undulation at the irradiation position of plant PT that is radiated by reference beam LS1 and measuring beam LS2 using diffuse reflection light RV1 of reference beam LS1 as reference data for detecting water or undulation at the irradiation position of plant PT, and using diffuse reflection light RV2 at the irradiation position of plant PT that is radiated by measuring beam LS2 and diffuse reflection light RV1 of reference beam LS1. Accordingly, plant stress detection camera 1 is able to detect water or undulation of plant PT with high precision using reference beam LS1 and measuring beam LS2 of two types of different wavelengths in measurement of distance from the camera to plant PT and in detection of water or undulation in plant PT, and diffuse reflection light RV1 and RV2 thereof.

Figure 8:
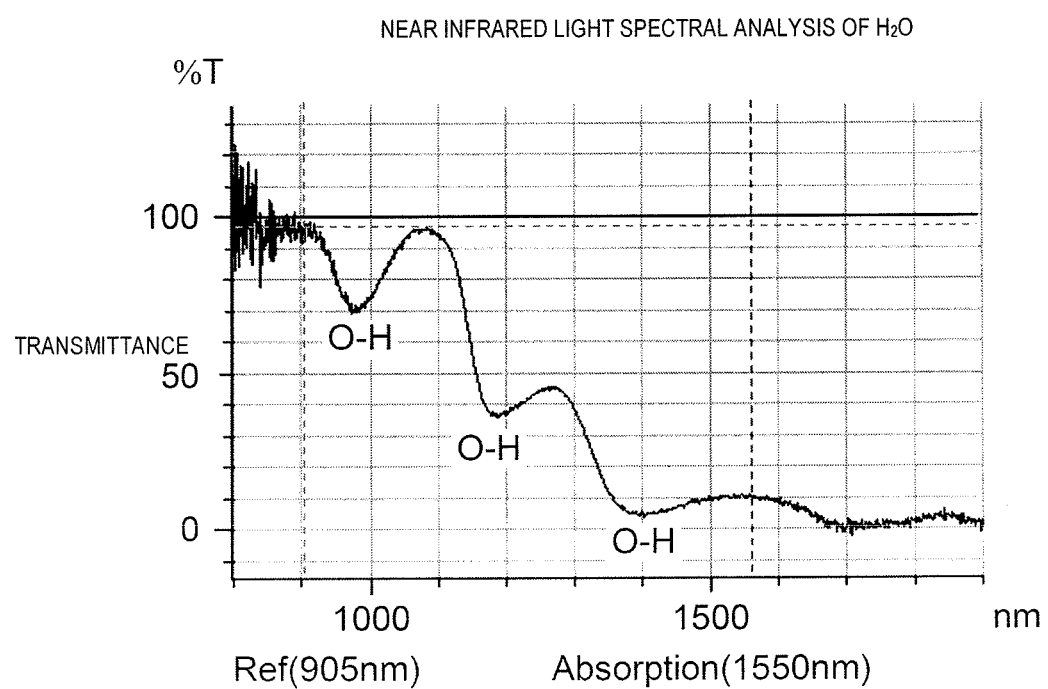
FIG. 8 is a graph illustrating an example of a near infrared spectra of water ($H_2O$)

FIG. 8 is a graph illustrating the near infrared spectra of water ($H_2O$). A horizontal axis of FIG. 8 indicates wavelength (nm), and a vertical axis of FIG. 8 indicates transmittance (transparency) (%). As shown in FIG. 8, since reference beam LS1 of wavelength 905 nm has transmittance in water ($H_2O$) that is close to 100%, it is understood that reference beam LS1 has a characteristic of tending not to be absorbed in water. In the same manner, since measuring beam LS2 of wavelength 1550 nm has transmittance in water ($H_2O$) that is close to 10%, it is understood that measuring beam LS2 has a characteristic of tending to be absorbed in water. Therefore, in the present embodiment, the wavelength of reference beam LS1 which is incident from first beam source 13 is 905 nm, and the wavelength of measuring beam LS2 which is incident from second beam source 15 is 1550 nm.

Figure 7:
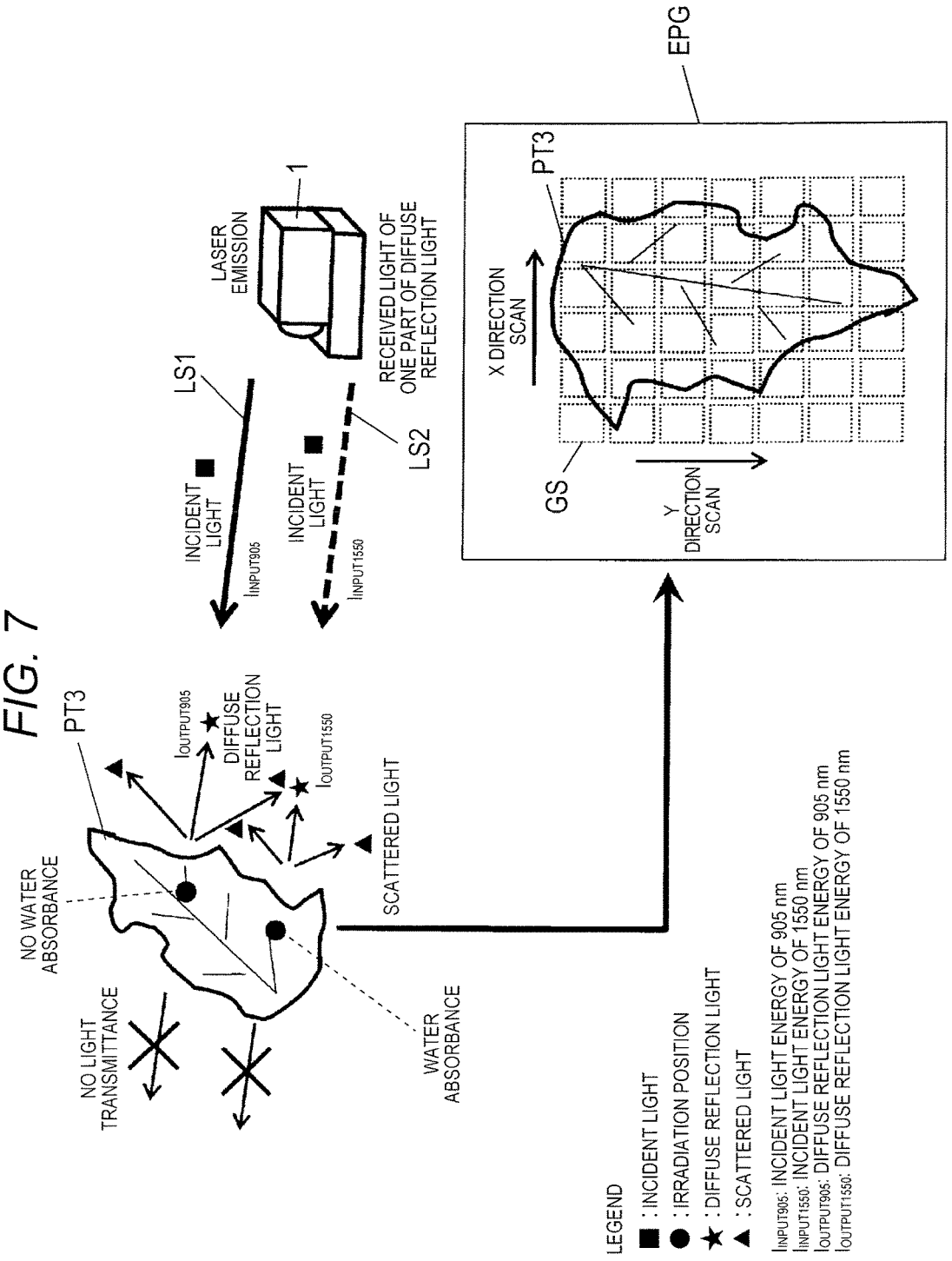
FIG. 7 is an operational overview which relates to radiation of the reference beam and the measuring beam on the plant of the plant stress detection camera of the present embodiment, and is an explanatory diagram of diffuse reflection light and scattered light generated by radiation at an irradiation position of the plant.

Beam scanner 17 two-dimensionally scans reference beam LS1 which is incident from first beam source 13 and measuring beam LS2 which is incident from second beam source 15 with respect to plant PT that is present in a detection area in invisible light sensor NVSS (refer to FIG. 7). Thereby, determiner JG is able to measure the distance from plant stress detection camera 1 to the irradiation position of reference beam LS1 of plant PT based on reflected diffuse reflection light RV1 at the irradiation position of reference beam LS1 on plant PT. Furthermore, plant stress detection camera 1 can detect presence or absence of water or undulation at the irradiation position of plant PT that is radiated by reference beam LS1 and measuring beam LS2 based on diffuse reflection light RV2 that is reflected at the irradiation position of plant PT by measuring beam LS2 and diffuse reflection light RV1 described above.

FIG. 7 is an operational overview which relates to radiation of reference beam LS1 and measuring beam LS2 on plant PT of plant stress detection camera 1 of the present embodiment, and is an explanatory diagram of diffuse reflection light RV1 and RV2 and scattered light generated by radiation at the irradiation position of plant PT. For ease of understanding of the description in FIG. 7, reference beam LS1 and measuring beam LS2 do not pass through leaf PT3, and the thickness of the shape of leaf PT3 is fixed to be flat (that is, there is no undulation). In FIG. 7, illustration is made such that the irradiation position of reference beam LS1 and irradiation position of measuring beam LS2 on leaf PT3 are different, but in practice, reference beam LS1 and measuring beam LS2 are radiated toward the same irradiation position except in a case where irradiation areas are different.

As shown in enlarged diagram EPG in FIG. 7, plant stress detection camera 1 scans in a two-dimensional direction of an X direction and a Y direction by laser emission and incidents by periodically alternately switches between reference beam LS1 and measuring beam LS2. Rectangular GS dotted line corresponds to one pixel of visible light camera image data that is imaged by plant stress detection camera 1. In enlarged diagram EPG, the visible light camera image data that reflects leaf PT3 of plant PT, has for example, an approximate total 6×7=42 pixels.

Plant stress detection camera 1 incidents by alternately switching between reference beam LS1 as incident light and measuring beam LS2 as incident light toward plant PT (in more detail, leaf PT3) that is the observation target by laser emission. As described above, since reference beam LS1 has a wavelength that has a characteristic of tending not to be absorbed in water, even in a case where there is water on the irradiation position of leaf PT3, reference beam LS1 is not absorbed, and diffuse reflection light RV1 (★ reference mark) and a plurality of scattered beams are generated due to radiation of reference beam LS1. Since measuring beam LS2 has a wavelength that has a characteristic of tending to be absorbed in water, in a case where there is water on the irradiation position of leaf PT3, measuring beam LS2 is partially absorbed, and diffuse reflection light RV2 (★ reference mark) that has lower intensity than the intensity of diffuse reflection light RV1 and a plurality of scattered beams are generated due to radiation of measuring beam LS2.

Here, balance of light energy that relates to reflectance on a front surface of leaf PT3 is described. Incident light energy of reference beam LS1 is described as "$I_{input905}$", incident light energy of measuring beam LS2 is described as "$I_{input1550}$", diffuse reflection light energy of diffuse reflection light RV1 is described as "$I_{output905}$", and diffuse reflection light energy of diffuse reflection light RV2 is described as "$I_{output1550}$".

A relationship is established such that "incident light energy" (fixed value) between reference beam LS1 and measuring beam LS2 and diffuse reflection lights RV1 and RV2 matches the sum of "energy that is lost due to absorption of water of leaf PT3 (● reference)", "diffuse reflection light energy (★ reference)", and "scattered light energy". It is possible to discriminate whether or not undulation is present in leaf PT3 by the amount of energy of scattered light. That is, when energy of the scattered light is great, since diffuse reflection light energy is low, undulation is present at the irradiation position of plant PT. Meanwhile, when energy of the scattered light is low, since diffuse reflection light energy is great, undulation is not present at the irradiation position of plant PT.

That is, plant stress detection camera 1 receives light of a part of diffuse reflection light RV1 and RV2 that is lowered in comparison to incident light energy of reference beam LS1 and measuring beam LS2 that is incident light due to influence of water or undulation that is present in leaf PT3. Wavelength 905 nm of reference beam LS1 and wavelength 1550 nm of measuring beam LS2 due to Lambert-Beer law are respectively established in Formula (1) and Formula (2).

Equation 1

$$\ln\left[\frac{I_{output1550}}{I_{input1550}}\right] = \alpha_{H_2O} \times C_{H_2O} \times t \quad (1)$$

Equation 2

$$\ln\left[\frac{I_{output905}}{I_{input905}}\right] = \alpha_{leaf} \times C_{leaf} \times t \quad (2)$$

In Formulas (1) and (2), $\alpha H_2O$ is a water-specific absorption coefficient (default value), $\alpha_{leaf}$ is a leaf-specific absorption coefficient (default value), t is a thickness of leaf PT3, $CH_2O$ is a concentration (variable) of water, and $C_{leaf}$ is a concentration (variable) of a component other than water. Formula (3) is established, and therefore an intensity ratio "$I_{output1550}/I_{output905}$" of diffuse reflection light RV1 and RV2 that is received by plant stress detection camera 1 established in Formula (4).

Equation 3

$$C_{H_2O} = 1 - C_{leaf} \quad (3)$$

Equation 4

$$\ln\left[\frac{I_{output1550}}{I_{output905}}\right] = (\alpha_{H_2O} + \alpha_{leaf}) \times t \times C_{H_2O} - \alpha_{leaf} \times t - \ln\left[\frac{I_{input1550}}{I_{input905}}\right] \quad (4)$$

Thereby, it is possible to calculate concentration of water $CH_2O$ of leaf PT3 at the irradiation position (that is, reflective position) by plant stress detection camera 1 calculating intensity ratio "$I_{output1550}/I_{output905}$" of diffuse reflection light RV1 and RV2 that is detected in detection processor 27 described later and substituting in Formula (4).

Figure 11:
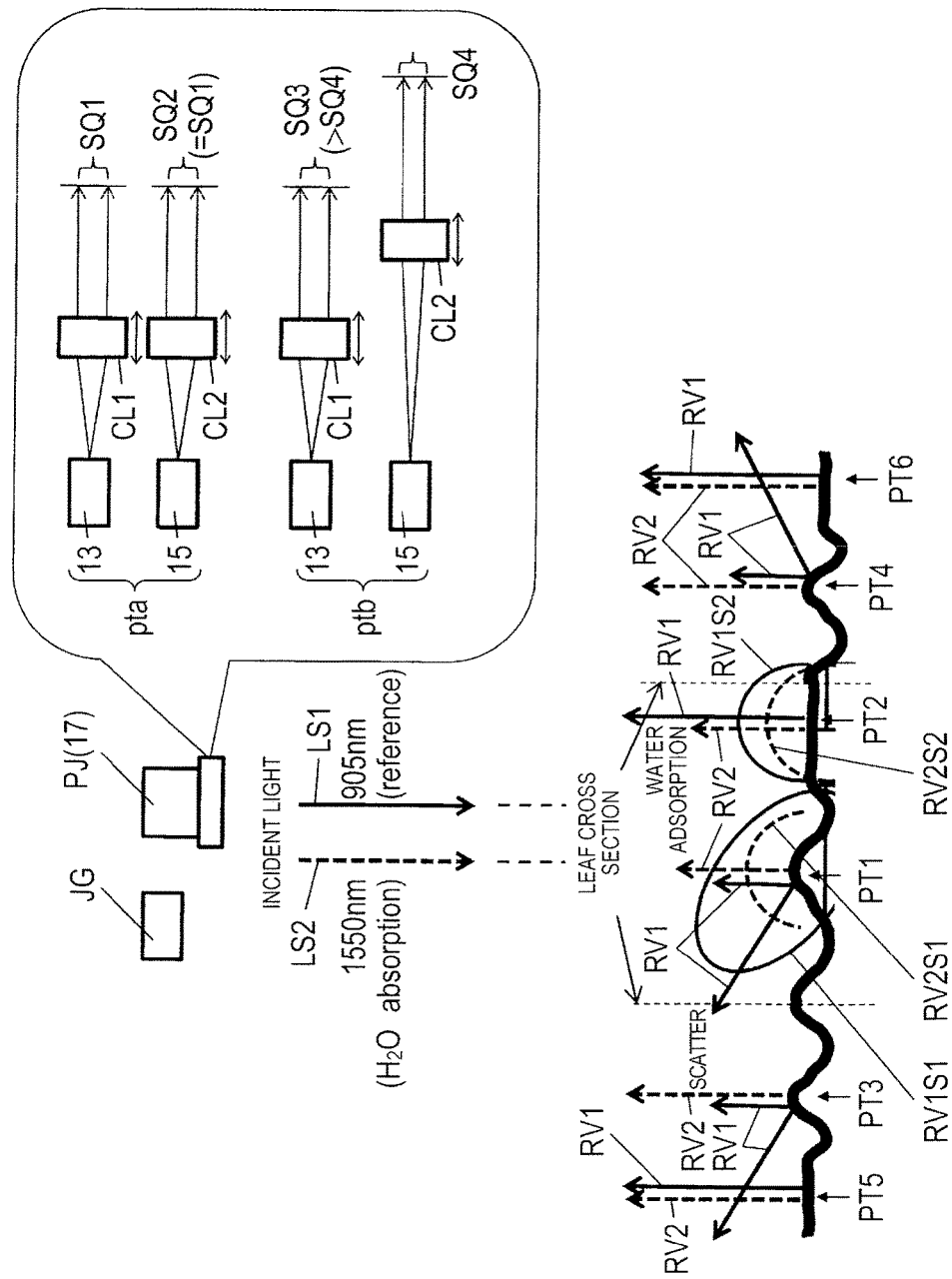
FIG. 11 is an explanatory diagram illustrating an example of presence or absence of water and undulation in a leaf of the plant and an intensity distribution of the diffuse reflection light of the reference beam and the measuring beam that are laser beams.

FIG. 11 is an explanatory diagram illustrating an example of presence or absence of water and undulation in leaf PT3 of plant PT and an intensity distribution of diffuse reflection light RV1 and RV2 of reference beam LS1 and measuring beam LS2 that are laser beams. Beam scanner 17 has first collimator lens CL1 that is movable in a paper surface left and right direction in FIG. 11 by a first motor within controller 11 described above and second collimator lens CL2 that is movable in a paper surface left and right direction in FIG. 11 by a second motor within controller 11 described above.

As shown in pattern pta in FIG. 11, in a case where a distance between first beam source 13 and first collimator lens CL1 and a distance between second beam source 15 and second collimator lens CL2 are the same, since the beam diameter of reference beam LS1 and measuring beam LS2 are the same, irradiation areas SQ1 and SQ2 of leaf PT3 of plant PT in which reference beam LS1 and measuring beam LS2 are irradiated are also the same. In other words, beam scanner 17 as an example of an irradiation setting unit sets the distance between first beam source 13 and first collimator lens CL1 and the distance between second beam source 15 and second collimator lens CL2 to be the same in pattern pta. Thereby, determiner JG of plant stress detection camera 1 is able to detect presence or absence of water at the irradiation positions of reference beam LS1 and measuring beam LS2 without receiving influence on presence or absence of undulation of leaf PT3.

Next, as shown in pattern ptb in FIG. 11, in a case where the distance between first beam source 13 and first collimator lens CL1 and the distance between second beam source 15 and second collimator lens CL2 are different, since the beam diameter of reference beam LS1 and measuring beam LS2 are different, irradiation areas SQ3 and SQ4 of leaf PT3 of plant PT in which reference beam LS1 and measuring beam LS2 are irradiated are also different. In other words, beam scanner 17 as an example of an irradiation setting unit sets the distance between first beam source 13 and first collimator lens CL1 and the distance between second beam source 15 and second collimator lens CL2 to be different in pattern ptb. Thereby, determiner JG of plant stress detection camera 1 is able to detect presence or absence of water at the irradiation positions of reference beam LS1 and measuring beam LS2 without receiving influence on presence or absence of undulation of leaf PT3 in a part in which the irradiation area is common. Determiner JG is able to detect presence or absence of undulation of leaf PT3 of plant PT based on an intensity ratio (refer to Formula (4)) of diffuse reflection light RV1 and RV2 that is reflected in different irradiation areas.

Next, as shown in FIG. 11, positions PT5 and PT6 are described at which there is no water or undulation in a cross section other than of leaf PT3 on which reference beam LS1 and measuring beam LS2 are irradiated. At positions PT5 and PT6, since reference beam LS1 and measuring beam LS2 do not receive influence of water or undulation, reference beam LS1 and measuring beam LS2 are similarly reflected, and the intensity ratio of diffuse reflection light RV1 and RV2 is the same as the intensity ratio of reference beam LS1 and measuring beam.

Next, positions PT3 and PT4 are described at which there is no water or there is or there is no undulation in a cross section other than of leaf PT3 on which reference beam LS1 and measuring beam LS2 are irradiated. For example, the irradiation position of reference beam LS1 is transitioned such that a light distribution characteristic of diffuse reflection light RV1 is set in an oblique direction (that is, a direction in which undulation is generated) since there is undulation, and intensity of diffuse reflection light RV1 that is received in determiner JG is lowered. Since the irradiation position of measuring beam LS2 is not transitioned such that a light distribution characteristic of diffuse reflection light RV2 is set in an oblique direction (that is, a direction in which undulation is generated) since there is no undulation, in comparison to a case where there is undulation, lowering of intensity of diffuse reflection light RV2 that is received in determiner JG is not observed.

Furthermore, positions PT1 and PT2 are described at which there is water and there is or there is no undulation in a cross section other than of leaf PT3 on which reference beam LS1 and measuring beam LS2 are irradiated. At position PT2, since there is water and there is no undulation, in comparison to a case where there is undulation without transitioning light distribution characteristic RV1S2 of diffuse reflection light RV1 of reference beam LS1 so as to be set in the oblique direction (that is, the direction in which undulation is generated), lowering of intensity of diffuse reflection light RV1 that is received in determiner JG is not observed. However, since light distribution characteristic RV2S2 of diffuse reflection light RV2 of measuring beam LS2 is not transitioned to the oblique direction (that is, the direction in which undulation is generated), but a part of measuring beam LS2 is absorbed in the water, intensity of diffuse reflection light RV2 is lowered.

At position PT1, since for example, there is water and undulation at the irradiation position of reference beam LS1, the irradiation position is transitioned such that light distribution characteristic RV1S1 of diffuse reflection light RV1 is set in the oblique direction (that is, the direction in which undulation is generated), and intensity of diffuse reflection light RV1 that is received in determiner JG is lowered. Since there is water but there is no undulation at the irradiation position of measuring beam LS2, light distribution characteristic RV2S1 of diffuse reflection light RV2 is not transitioned to in the oblique direction (that is, the direction in which undulation is generated), and there is no lowering of intensity of diffuse reflection light RV2 that is caused by there being undulation, but since a part of measuring beam LS2 is absorbed in water that is present at position PT1, intensity of diffuse reflection light RV2 is lowered.

Next, an internal configuration of determiner JG is described in detail with reference to FIGS. 2 and 3.

Figure 3:
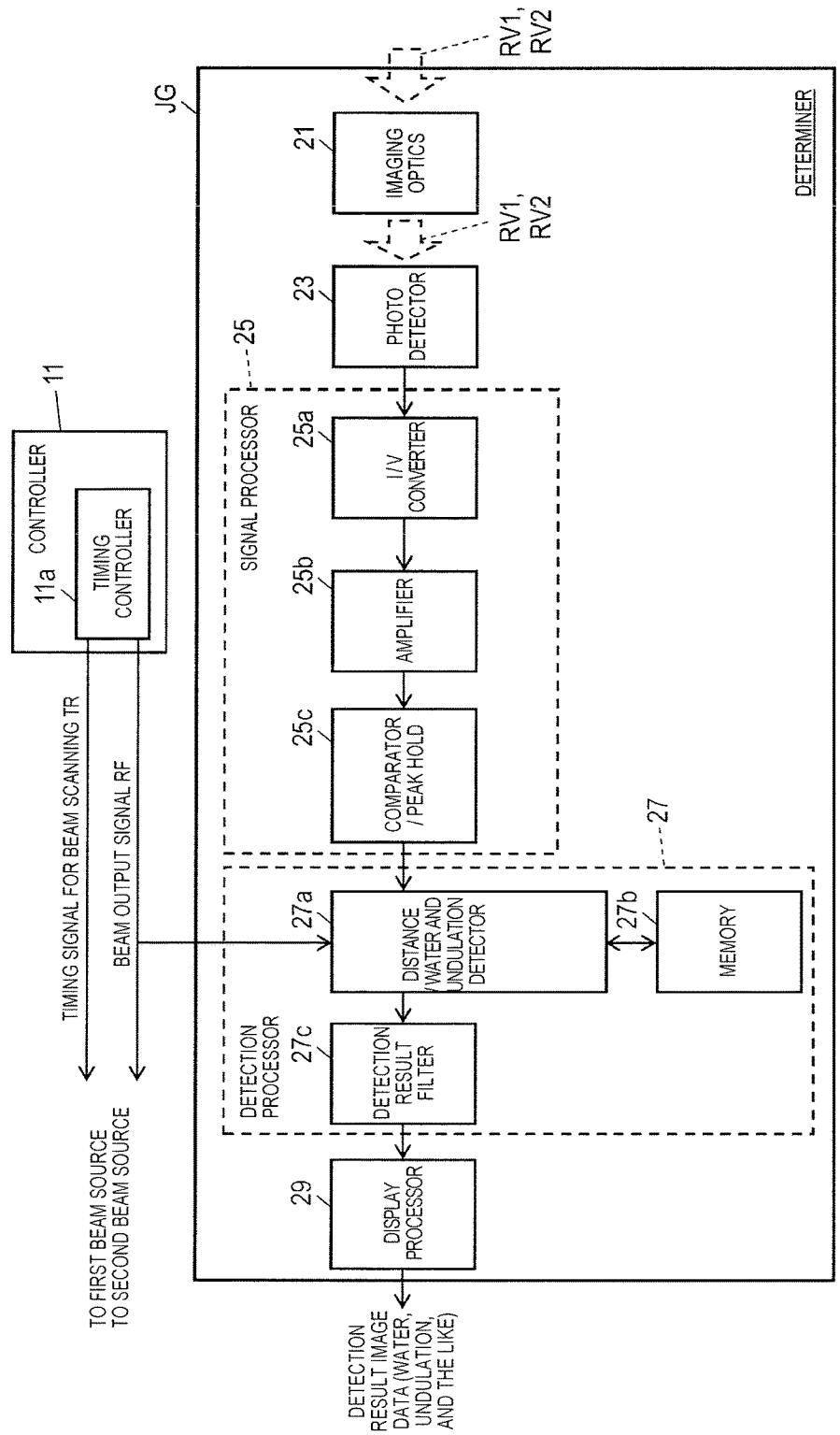
FIG. 3 is a block diagram illustrating in detail an example of an internal configuration of a determiner of the plant stress detection camera in the embodiment.

FIG. 3 is a block diagram illustrating in detail an example of an internal configuration of a determiner JG of plant stress detection camera 1.

Imaging optics 21 is configured using, for example, a lens, light (for example, diffuse reflection light RV1 or diffuse reflection light RV2) which is incident from outside of plant stress detection camera 1 is concentrated, and diffuse reflection light RV1 or diffuse reflection light RV2 form an image on a predetermined imaging area of photo detector 23.

Photo detector 23 is an image sensor which has a peak of spectral sensitivity with respect to wavelengths of both of reference beam LS1 and measuring beam LS2. Photo detector 23 converts an optical image of diffuse reflection light RV1 or diffuse reflection light RV2 that form an image on the imaging area to an electrical signal. Output of photo detector 23 is input to signal processor 25 as the electrical signal (current signal). Imaging optics 21 and photo detector 23 functions as an imaging unit in invisible light sensor NVSS.

Signal processor 25 has I/V converter 25a, amplifier 25b, and comparator/peak hold 25c. I/V converter 25a converts the current signal that is an output signal (analog signal) of photo detector 23 to a voltage signal. Amplifier 25b amplifies a level of the voltage signal that is the output signal (analog signal) of I/V converter 25a up to a processable level in comparator/peak hold 25c.

Comparator/peak hold 25c binarizes the output signal of amplifier 25b and outputs to distance/water and undulation detector 27a according to a comparative result of the output signal (analog signal) of amplifier 25b and the predetermined threshold level. In addition, comparator/peak hold 25c includes an analog digital converter (ADC), detects and holds the peak of an analog digital (AD) converter result of the output signal (analog signal) of amplifier 25b and furthermore, outputs peak information to distance/water and undulation detector 27a.

Detection processor 27 as an example of the detector has distance/water and undulation detector 27a, memory 27b, and detection result filter 27c. Distance/water and undulation detector 27a measures the distance from plant stress detection camera 1 to the irradiation position of reference beam LS1 of plant PT based on output (binary signal) from comparator/peak hold 25c in diffuse reflection light RV1 of reference beam LS1 that has the first wavelength (for example, 905 nm).

Figure 5A:
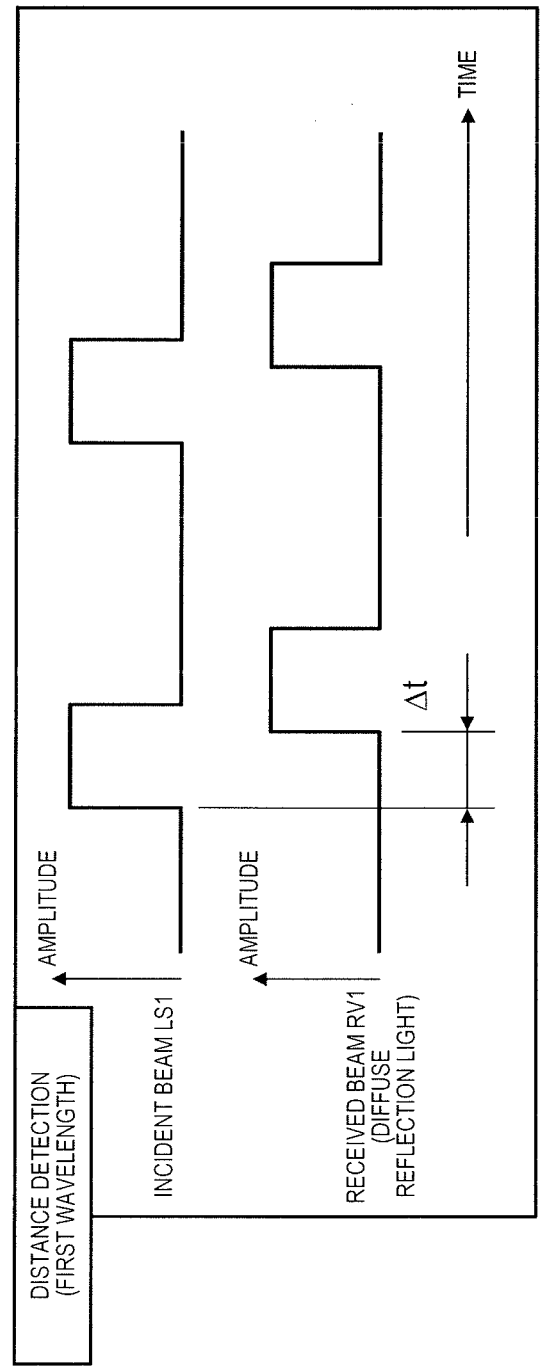
FIG. 5A is a principle explanatory diagram of distance detection in which a reference beam of a first wavelength (for example, 905 nm) is used out of two types of different wavelengths (for example, 905 nm and 1550 nm) of an invisible light sensor.

In detail, distance/water and undulation detector 27a measures the distance from plant stress detection camera 1 to the irradiation position of reference beam LS1 of plant PT based on time difference Δt (refer to FIG. 5A) from an incident time of reference beam LS1 until a light reception time of diffuse reflection light RV1. FIG. 5A is a principle explanatory diagram of distance detection in which a reference beam LS1 of a first wavelength (for example, 905 nm) is used out of two types of different wavelengths (for example, 905 nm and 1550 nm) of an invisible light sensor NVSS.

Distance/water and undulation detector 27a determines an input time of beam output signal RF from timing controller 11*a* as the incident time of reference beam LS1, and determines the input time of output from comparator/peak hold 25*c* as the light reception time of diffuse reflection light RV1. Distance/water and undulation detector 27*a* easily obtains the distance from plant stress detection camera 1 to the irradiation position of reference beam of plant PT by calculating, for example, the distance as "distance=light velocity×(time difference Δt/2)". Output of comparator/peak hold 25*c* is necessary in diffuse reflection light RV1 of reference beam LS1 of at least one type of wavelength in measurement of the distance in distance/water and undulation detector 27*a*. Distance/water and undulation detector 27*a* outputs distance information to detection result filter 27*c*.

Distance/water and undulation detector 27*a* detects presence or absence of water and undulation at the irradiation position of reference beam LS1 and measuring beam LS2 of plant PT based on output (peak information) of comparator/peak hold 25*c* in diffuse reflection beam RV1 of reference beam LS1 and output (peak information) of comparator/peak hold 25*c* in diffuse reflection beam RV2 of measuring beam LS2.

In detail, distance/water and undulation detector 27*a* temporarily stores, for example, output (peak information) of comparator/peak hold 25*c* in diffuse reflection beam RV1 of reference beam LS1 in memory 27*b*, and next, waits until the output (peak information) of comparator/peak hold 25*c* in diffuse reflection beam RV2 of measuring beam LS2 is obtained. Distance/water and undulation detector 27*a* obtains output (peak information) of comparator/peak hold 25*c* in diffuse reflection beam RV2 of measuring beam LS2, and then calculates a ratio of output (peak information) of comparator/peak hold 25*c* in diffuse reflection beam RV1 of reference beam LS1 and output (peak information) of comparator/peak hold 25*c* in diffuse reflection light RV2 of measuring beam LS2 in the same line of plant PT that are contained in the angle of view with reference to memory 27*b*.

Figure 5B:
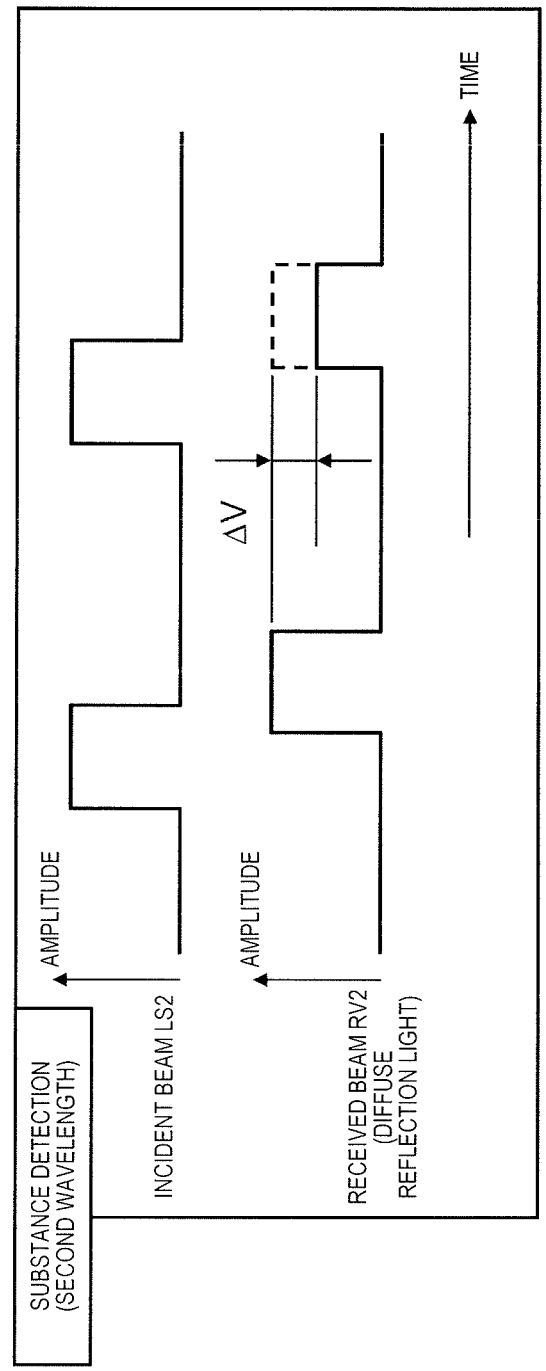
FIG. 5B is a principle explanatory diagram of water detection in which the reference beam and a measuring beam are used of the two types of different wavelengths (for example, 905 nm and 1550 nm) of the invisible light sensor.

For example, at the irradiation position at which there is water, since a part of measuring beam LS2 tends to be absorbed, intensity (that is, amplitude) of diffuse reflection beam RV2 is attenuated (refer to FIG. 5B). FIG. 5B is a principle explanatory diagram of water detection in which the reference beam LS1 and a measuring beam LS2 are used of the two types of different wavelengths (for example, 905 nm and 1550 nm) of the invisible light sensor NVSS. Accordingly, it is possible for distance/water and undulation detector 27*a* to detect presence or absence of water or undulation at the irradiation position of reference beam LS1 and measuring beam LS2 based on a calculation result (for example, calculation result of difference (difference ΔV of amplitude) of each intensity of diffuse reflection beam RV1 and diffuse reflection beam RV2 or intensity ratio of diffuse reflection beam RV1 and diffuse reflection beam RV2) of each line of plant PT which is contained in the angle of view.

Distance/water and undulation detector 27*a* may detect presence or absence of water or undulation at the irradiation position of reference beam LS1 and measuring beam LS2 of plant PT (refer to FIG. 6) according to a comparison of the size of ratio R of amplitude difference between amplitude VA of diffuse reflection beam RV1 of reference beam LS1 and amplitude VB of diffuse reflection beam RV2 of measuring beam LS2 (VA−VB) and amplitude VA with predetermined detection threshold level M. FIG. 6 is a principle explanatory diagram of detection of water or undulation in an invisible light sensor NVSS. For example, distance/water and undulation detector 27*a* may determine that water is detected if R>M, and may determine that water is not detected if R≤M. In this manner, distance/water and undulation detector 27*a* is able to eliminate influence of noise (for example, disturbance light) and is able to detect presence or absence of water or undulation with high precision by detecting presence or absence of water or undulation according to a comparative result of ratio R between amplitude difference (VA−VB) and amplitude VA and detection threshold level M.

Memory 27*b* is configured using, for example, a random access memory (RAM), and temporarily stores output (peak information) of comparator/peak hold 25*c* in diffuse reflection beam RV1 of reference beam LS1.

Detection result filter 27*c* filters and extracts information which relates to the detection result of water or undulation in which the distance from plant stress detection camera 1 is within a detection target distance or a detection target distance range based on output of distance/water and undulation detector 27*a* and information on a predetermined detection target distance or the detection target distance range that is designated from controller 11. Detection result filter 27*c* outputs information which relates to the extraction result to display processor 29. For example, detection result filter 27*c* outputs information which relates to the extraction result of water and undulation at the irradiation position of reference beam LS1 and measuring beam LS2 of plant PT as well as distance information from plant stress detection camera 1 to display processor 29.

Display processor 29 uses output of detection result filter 27*c* and generates detection result image data that indicates the position of water or undulation at the irradiation position at each distance from plant stress detection camera 1 as an example of information which relates to water or undulation at the irradiation position in which the distance from plant stress detection camera 1 is in the detection target distance or the detection target distance range. Display processor 29 outputs detection result image data which includes information on distance from plant stress detection camera 1 to the irradiation position to display controller 37 of visible light camera VSC.

Next, each part of visible light camera VSC will be described.

Imaging optics 31 is configured using, for example, a lens, ambient light RV0 from in the angle of view of plant stress detection camera 1 is concentrated, and ambient light RV0 forms an image on a predetermined imaging area of photo detector 33.

Photo detector 33 is an image sensor which has a peak of spectral sensitivity with respect to wavelength of visible light (for example, 0.4 to 0.7 μm). Photo detector 33 converts an optical image that forms an image on the imaging surface to the electrical signal. Output of photo detector 33 is input to image signal processor 35 as the electrical signal. Imaging optics 31 and photo detector 33 function as an imaging unit in visible light camera VSC.

Image signal processor 35 uses the electrical signal which is output of photo detector 33, and visible light image data is generated which is specified by a person in recognizable red, green, and blue (RGB), brightness and color difference (YUV), and the like. Thereby, visible light image data that is imaged by visible light camera VSC forms visible light camera image data. Image signal processor 35 outputs visible light image data to display controller 37.

In a case where display controller 37 as an example of the display data generator uses visible light image data that is output from image signal processor 35 and detection result image data that is output from display processor 29, and detects water or undulation at any position of the visible light image data, display data in which visible light image data and detection result image data are composited, or display data which comparatively represents the visible light image data and detection result image data are generated as examples of information related to water or undulation. Display controller 37 (output unit) prompts display by transmitting display data to data logger DL or communication terminal MT that are connected via, for example, a network. Details of a display data generation process in display controller 37 will be described later with reference to FIG. 10.

Controller 11 may modify the detection target distance or the detection target detection range as an example of set distance information that is set in detection processor 27. The modification of the detection target distance range may be performed automatically by controller 11 and may be performed at an arbitrary timing by a user using communication terminal MT and the like. Thereby, it is possible to set an appropriate detection target distance or detection target distance range according to an environment in which plant stress detection camera 1 is installed. The set distance information is the detection target distance that is set in advance, for example, in detection result filter 27c of detection processor 27.

Controller 11 may modify a value in the detection target distance range that is calculated according to the value of the detection target distance in a case where the detection target distance range is calculated based on information on the detection target distance that is input by data logger DL or communication terminal MT. In a case where distance to the detection target is large, since attenuation of intensity (amplitude) of the diffuse reflection light in comparison to a case where the distance to the detection target is small is large, an amount of errors during distance detection in distance/water and undulation detector 27a is increased. It is preferable that controller 11 increases the calculated detection target distance range the larger the value of the input detection target distance. For example, in a case where the detection target distance that is output from controller 11 is 3 [m], detection processor 27 modifies the detection target distance range to 2 to 4 [m]. In a case where the detection target distance that is output from controller 11 is 100 [m], detection processor 27 modifies the detection target distance range to 95 to 105 [m]. Thereby, plant stress detection camera 1 is able to set the appropriate detection target distance range according to the distance to the detection target. Accordingly, display controller 37 is able to generate display data as an example of information which relates to a specific material considering errors during distance detection in detection processor 27 according to the length of the detection target distance. Plant stress detection camera 1 is able to detect the specific material in a case where the distance from plant stress detection camera 1 to plant PT does not completely match the detection target distance output from controller 11 by setting the detection target distance range.

Data logger DL transmits display data that is output from display controller 37 to communication terminal MT or one or more externally connected device (not illustrated), and prompts display of display data on a display screen of communication terminal MT or one or more externally connected device (for example, monitor 50 within the control room in the office indicated in FIG. 1). Data logger DL transmits information on the detection target distance or the detection target distance range of water or undulation that are sent by an input operation of the user of communication terminal MT or one or more externally connected device to plant stress detection camera 1. The information on the detection target distance or the detection target distance range of water or undulation is input to controller 11. Thereby, data logger DL is able to input information on the detection target distance or the detection target distance range of water or undulation that are designated by the input operation of the user to plant stress detection camera 1. The detection target distance range of water or undulation that are input to one of water or undulation from data logger DL may be a plurality of ranges, and furthermore, a set number of a plurality of detection target distance ranges may be arbitrarily input. Thereby, data logger DL is able to arbitrarily set a desired detection target distance range or the set number of detection target distance ranges by the user to plant stress detection camera 1.

Communication terminal MT is, for example, a portable communication terminal which is used by an individual user, receives display data that is transmitted from display controller 37 via the network (not illustrated), and displays display data on the display screen (not illustrated) of communication terminal MT. Communication terminal MT transmits information on the detection target distance or the detection target distance range of water or undulation to plant stress detection camera 1 via or directly to data logger DL in a case where the information on the detection target distance of water or undulation is input by the input operation of the user. In the same manner, the information on the detection target distance or the detection target distance range of water or undulation is input to controller 11. Thereby, communication terminal MT is able to input information on the detection target distance or the detection target distance range of water or undulation that are designated by the input operation of the user to plant stress detection camera 1 via or directly to data logger DL. The detection target distance range of water or undulation that are input to plant stress detection camera 1 from communication terminal MT may be a plurality of ranges, and furthermore, the set number of the plurality of detection target distance ranges may be arbitrarily input. Thereby, communication terminal MT is able to arbitrarily set the desired detection target distance range or the set number of detection target distance ranges by the user to plant stress detection camera 1.

In a case where detection target distance range is input by the input operation of the user, controller 11 may be set to detection processor 27 without modifying the input detection target distance range. Alternatively, controller 11 that is an example of a calculation unit may calculate the detection target distance range that is set to detection processor 27 and may set to detection processor 27 based on the input detection target distance range. For example, in a case where 4 to 7 [m] is input as the detection target distance range by the input range of the user, controller 11 may be set to detection processor 27 by modifying the detection target distance range to 5 to 6 [m], 3 to 8 [m], and the like.

Figure 4:
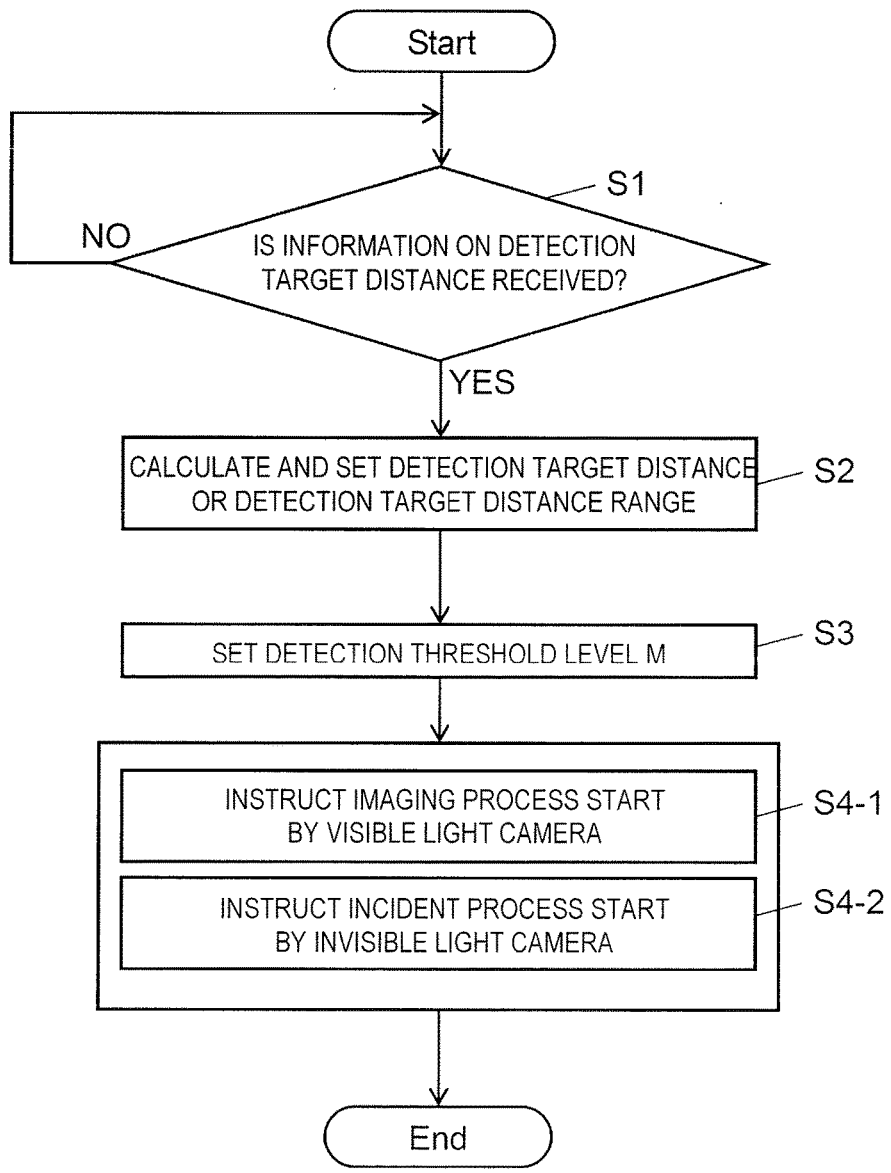
FIG. 4 is a flowchart illustrating an example of an initial operation in a controller of the plant stress detection camera in the embodiment.

Description of Example of Initial Operation in Invisible Light Sensor Controller Next, an example of an initial operation in controller 11 of invisible light sensor NVSS of plant stress detection camera 1 of the present embodiment will be described with reference to FIG. 4. FIG. 4 is a flow chart illustrating an example of an initial setting operation in controller 11 of plant stress detection camera 1.

In FIG. 4, in a case where information on the detection target distance of water or undulation that is sent by plant stress detection camera 1 from data logger DL or communication terminal MT is received (S1, YES), controller 11 acquires the information on the detection target distance of water or undulation. Controller 11 calculates the detection target distance range of water or undulation in which invisible light sensor NVSS is the detection target based on the information of the detection target distance of water or undulation, and the information on the acquired detection target distance or the calculated detection target distance range is set to signal processor 25 or detection processor 27 (S2).

For example, information on the distance or the direction from plant stress detection camera 1 to the detection target that is water of undulation, set condition information on plant stress detection camera 1, or the like are included in information on the detection target distance of water or undulation. The information on the distance from plant stress detection camera 1 may be a predetermined value, and may be arbitrarily set by the user utilizing communication terminal MT and the like. The set condition information on plant stress detection camera 1 may be set in advance in plant stress detection camera 1 and may be arbitrarily set by the user utilizing communication terminal MT and the like. The set condition information is, for example, information on the height of plant stress detection camera 1 from the ground, incident angle of plant stress detection camera 1, the breadth of an installation room, and the like. In plant stress detection camera 1 to which set condition information is input, for example, controller 11 may calculate the detection target distance or the target distance range of water or undulation based on the set condition information. It is possible to detect water or undulation according to the set environment and it is possible to suppress false detection by setting such set condition information.

Controller 11 may modify the detection target distance range that is calculated in step S2 according to information on height of plant stress detection camera 1 from a predetermined surface (for example, floor FL). The modification of the detection target distance range may be performed automatically by controller 11 and may be performed at an arbitrary timing by a user using communication terminal MT and the like. The detection target distance range may be directly input by data logger DL, communicator terminal MT, or the like without calculation based on the detection target distance. Alternatively, plant stress detection camera 1 may be provided with an input unit that is able to input the detection target distance or the detection target distance range.

In a case where distance to the detection target is large, since attenuation of intensity (amplitude) of the diffuse reflection light in comparison to a case where the distance to the detection target is small is large, an amount of errors during distance detection in distance/water and undulation detector 27a is increased. Therefore, it is preferable that the more controller 11 increases the input height information, the larger the calculated detection target distance range. Thereby, it is possible for plant stress detection camera 1 to further improve detection precision of water or undulation in invisible light sensor NVSS considering errors during distance detection in invisible light sensor NVSS by modifying the detection target distance range according to a case where, for example, the height information from the predetermined surface of plant stress detection camera 1 is small (for example, 3 [m]) or in a case of being large (for example, 100 [m]). Display controller 37 is able to generate display data as an example of information which relates to water or undulation considering errors during distance detection in detection processor 27 according to the height at which plant stress detection camera 1 is installed.

In addition, controller 11 sets detection threshold level M of water or undulation in detection processor 27 of invisible light sensor NVSS in distance/water and undulation detector 27a of detection processor 27 (S3). It is preferable to appropriately provide detection threshold level M according to a specific material that is a detection target.

After the process of step S3, controller 11 outputs a control signal for starting an imaging process to each part of visible light camera VSC (S4-1), and furthermore, outputs to first beam source 13 and second beam source 15 of invisible light sensor NVSS timing signal for beam scanning TR for starting incidence of reference beam LS1 and measuring beam LS2 to first beam source 13 and second beam source 15 (S4-2). Either an execution timing of an operation of step S4-1 or an execution timing of an operation of step S4-2 may be first, or may be simultaneous.

Figure 9:
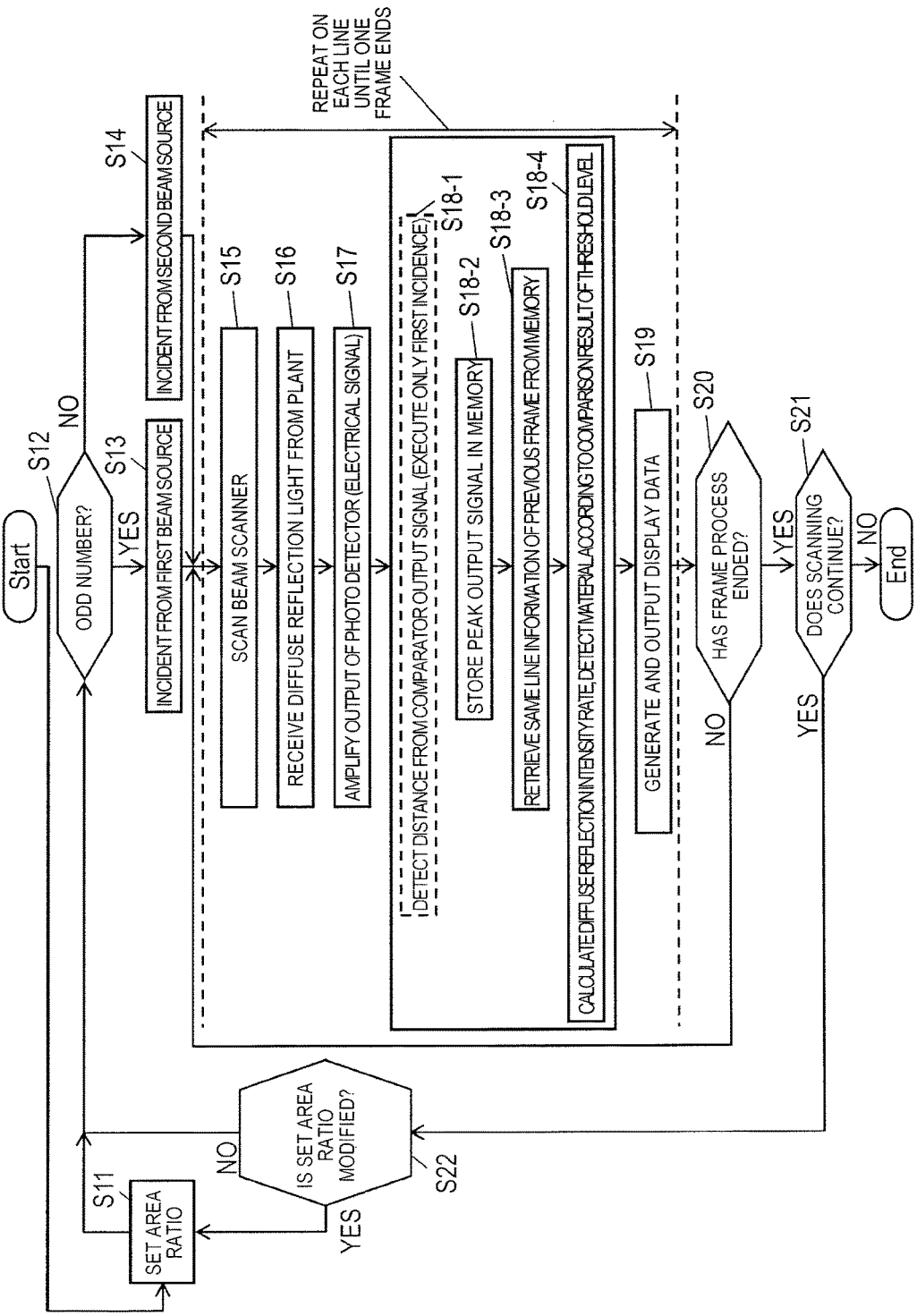
FIG. 9 is a flow chart illustrating an example of a detailed operation procedure which relates to detection of water or undulation of plant in the invisible light sensor.

Description of Detailed Operation Relating to Detection of Water or Undulation of Invisible Light Sensor Next, a detailed operation procedure which relates to detection of water or undulation in invisible light sensor NVSS of plant stress detection camera 1 will be described with reference to FIG. 9. FIG. 9 is a flow chart illustrating a detailed operation procedure which relates to detection of water or undulation of plant PT in invisible light sensor NVSS. As a premise of description of the flow chart illustrated in FIG. 9, timing controller 11a outputs timing signal for beam scanning TR to first beam source 13 and second beam source 15, and reference beam LS1 and measuring beam LS2 from plant stress detection camera 1 is radiated toward leaf PT3 of plant PT.

In FIG. 9, controller 11 sets the irradiation area of leaf PT3 on which reference beam LS1 is irradiated and the irradiation area of leaf PT3 on which measuring beam LS2 is irradiated so as to have the same or different values (S11). As described above, in order to detect only water of leaf PT3, the irradiation area of leaf PT3 on which reference beam LS1 is irradiated and the irradiation area of leaf PT3 on which measuring beam LS2 is irradiated are set so as to be the same. In order to detect water or undulation of leaf PT3, the irradiation area of leaf PT3 on which reference beam LS1 is irradiated and the irradiation area of leaf PT3 on which measuring beam LS2 is irradiated are set so as to be different.

After step S11, in a case where controller 11 determines that beam output signal RF in incidence period of an odd number of times is output from timing controller 11a (S12, YES), first beam source 13 incidents reference beam LS1 according to beam output signal RF from timing controller 11a (S13). Beam scanner 17 one-dimensionally scans reference beam LS1 of one line or more in an X direction of plant PT which is contained in the angle of view of plant stress detection camera 1 (S15, refer to enlarged diagram EPG in FIG. 7). At the irradiation position on each line in the X direction on which the reference beam LS1 is radiated, diffuse reflection light RV1 that is generated by reference beam LS1 being diffused and reflected is received by photo detector 23 via imaging optics 21 (S16).

In signal processor 25, output (electrical signal) in photo detector 23 of diffuse reflection light RV1 is converted to the voltage signal, and the level of the electrical signal is amplified up to a processable level in comparator/peak hold 25c (S17). Comparator/peak hold 25c binarizes the output signal of amplifier 25b and outputs to distance/water and undulation detector 27a according to a comparative result of the output signal of amplifier 25b and the predetermined threshold level. Comparator/peak hold 25c outputs peak information of output signal of amplifier 25b to distance/water and undulation detector 27a.

Distance/water and undulation detector 27a measures the distance from plant stress detection camera 1 to the irradiation position (that is, reflection position) based on output (binary signal) from comparator/peak hold 25c in diffuse reflection light RV1 of reference beam LS1 (S18-1). The process of step S18-1 may be omitted.

Distance/water and undulation detector 27a temporarily stores output (peak information) of comparator/peak hold 25c with respect to diffuse reflection light RV1 of reference beam LS1 in memory 27b (S18-2). In addition, distance/water and undulation detector 27a reads from memory 27b output of comparator/peak hold 25c with respect to the same line in diffuse reflection light RV1 or diffuse reflection light RV2 with respect to reference beam LS1 or measuring beam LS2 in a previous frame (incidence period) that is stored in memory 27b (S18-3). Distance/water and undulation detector 27a detects presence or absence of water and undulation on the same line based on output (peak information) of comparator/peak hold 25c in diffuse reflection light RV1 of reference beam LS1 and output (peak information) of comparator/peak hold 25c in diffuse reflection light RV2 of measuring beam LS2 on the same line and predetermined detection threshold level M (S18-4). Detection result filter 27c filters and extracts information which relates to water or undulation in which the distance from plant stress detection camera 1 is within a detection target distance or a detection target distance range based on output of distance/water and undulation detector 27a and information on a predetermined detection target distance or the detection target distance range that is designated from controller 11.

Display processor 29 uses output of detection result filter 27c and generates detection result image data that indicates the detection position of water or undulation at each distance from plant stress detection camera 1 as an example of information which relates to water or undulation in which the distance from plant stress detection camera 1 is the detection target distance or the detection target distance range (S19). Each operation of steps S15, S16, S17, S18-1 to S18-4, and S19 is executed in each line within the detection area of one frame (incidence period).

That is, when each operation of steps S15, S16, S17, S18-1 to S18-4, and S19 is complete with respect to one line in the X direction, each operation of steps S15, S16, S17, S18-1 to S18-4, and S19 is performed with respect to a subsequent line in the X direction (S20, NO), hereinafter until each operation of steps S15, S16, S17, S18-1 to S18-4, and S19 is complete in one frame, each operation of steps S15, S16, S17, S18-1 to S18-4, and S19 is repeated with respect to scanning in a Y direction indicated in enlarged diagram EPG in FIGS. 7A and 7B.

Meanwhile, in a case where execution of each operation of steps S15, S16, S17, S18-1 to S18-4, and S19 is complete with respect to all lines in one frame (S20, YES), and in a case where scanning of an incident beam is continued (S21, YES), the operation of invisible light sensor NVSS proceeds to step S22. That is, in a case of being set such that the ratio (area ratio) between the irradiation area of leaf PT3 on which reference beam LS1 is irradiated and the irradiation area of leaf PT3 on which measuring beam LS2 is irradiated is modified (S22, YES), controller 11 sets such that the area ratio between the irradiation area of leaf PT3 on which reference beam LS1 is irradiated and the irradiation area of leaf PT3 on which measuring beam LS2 is irradiated is the area ratio after modification (S11). Meanwhile, in a case where the ratio (area ratio) between the irradiation area of leaf PT3 on which reference beam LS1 is irradiated and the irradiation area of leaf PT3 on which measuring beam LS2 is irradiated is not modified (S22, NO), since there is a subsequent incident period (that is, an incident period of an even number) (S12, NO), second beam source 15 incidents measuring beam LS2 according to beam output signal RF from timing controller 11a (S14). Description of subsequent steps to step S14 is the same as the description of subsequent steps to step S14 described above and is therefore omitted. Meanwhile, in a case where scanning of reference beam LS1 and measuring beam LS2 is not continued (S21, NO), the operation of invisible light sensor NVSS is complete.

Description of Display Data Generation

Figure 10:
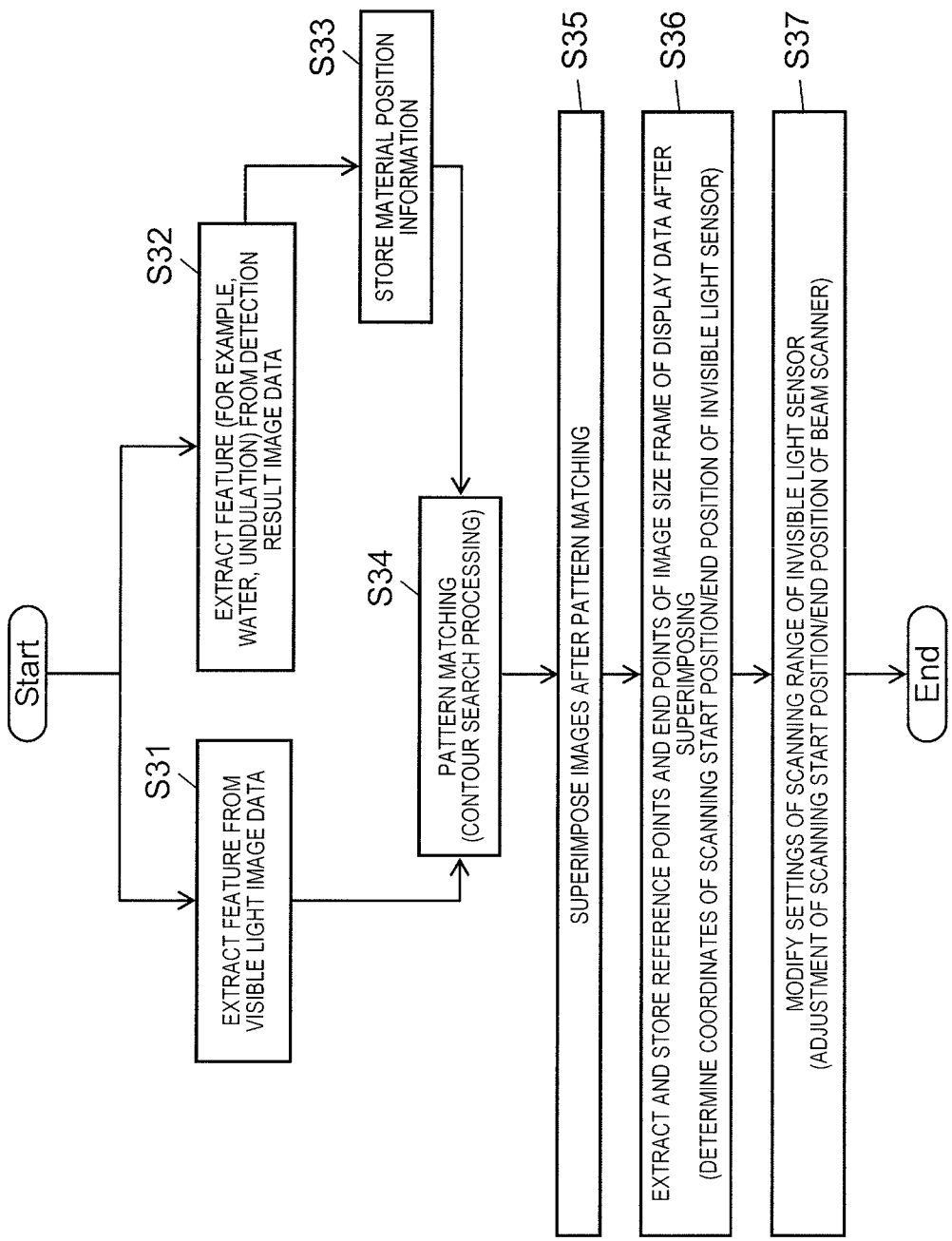
FIG. 10 is a flow chart illustrating an example of a detailed operation procedure of calibration of an output image size in a display controller of the plant stress detection camera of the present embodiment.

Next, the display data generation process in display controller 37 will be described in detail with reference to FIG. 10. FIG. 10 is a flow chart illustrating an example of a detailed operation procedure of calibration of an output image size in display controller 37 of plant stress detection camera 1 of the present embodiment. Description in FIG. 10 is description which relates to calibration that is performed when display controller 37 composites both image data sets such that each size of visible light camera image data and detection result image data match.

Plant stress detection camera 1 in the present embodiment is configured such that visible light camera VSC and invisible light sensor NVSS are integrally combined, but another configuration of each part is the same as an existing monitoring camera except for display controller 37 of visible light camera VSC in the present embodiment. In this case, invisible light sensor NVSS of plant stress detection camera 1 in the present embodiment is configured in addition to existing visible light camera VSC. Accordingly, a case is considered in which an aspect ratio of visible light image data that is imaged by visible light camera VSC and an aspect ratio of detection result image data that is generated by invisible light sensor NVSS do not match. In the calibration illustrated in FIG. 10, display controller 37 matches an aspect ratio of visible light image data that is imaged by visible light camera VSC and an aspect ratio of detection result image data that is generated by invisible light sensor NVSS.

In FIG. 10, display controller 37 extracts a feature of visible light image data by a filtering process that uses, for example, color information (S31). The operation of step S31 may be executed by image signal processor 35, and in this case, display controller 37 acquires information on the feature extraction result of visible light image data that is executed by image signal processor 35 from image signal processor 35.

Display controller 37 extracts a feature of detection result image data by a filtering process that uses, for example, each set of distance information (S32). The operation of step S32 may be executed by display processor 29, and in this case, display controller 37 acquires information on the feature extraction result of detection result image data that is executed by display processor 29 from display processor 29. Display controller 37 stores information which relates to a detection position of the extracted water or undulation in a memory (not illustrated) for work memory based on the feature extraction result of the detection result image data that is obtained using step S32 (S33).

Display controller 37 executes pattern matching by searching each contour of the visible light image data and the detection result image data using information on the feature extraction result of the visible light image data that is obtained in step S31 and information on the feature extraction result of the detection result image data that is obtained in step S32 (S34). Display controller 37 superimposes the visible light image data and the detection result image data after the pattern matching in step S34 (S35). According to step S34 and step S35, display controller 37 is able to obtain display data that superimposes the visible light image data and the detection result image data where the aspect ratios match.

Display controller 37 extracts reference points (for example, origins) and end points of an image size frame of display data after the superimposing in step S35 and stores in controller 11 (S36). In FIG. 2, in order to avoid complication of the drawings, illustration of arrows between controller 11 and display controller 37 is omitted. Reference points and end points of the image size frame of the display data correspond to a scanning start position and a scanning end position of the incident beam from invisible light sensor NVSS.

After step S36, controller 11 modifies a scanning range of the incident beam in invisible light sensor NVSS using the reference points (for example, origins) and the end points of the image size frame of display data that is acquired from display controller 37 and sets information on the scanning start position and the scanning end position of the incident beam of beam scanner 17 after modification to beam scanner 17 (S37). By executing the calibration illustrated in FIG. 10 once, display controller 37 is able to easily generate display data in which the aspect ratio of the visible light image data from visible light camera VSC and the aspect ratio of the detection result image data from invisible light sensor NVSS match.

Figure 12:
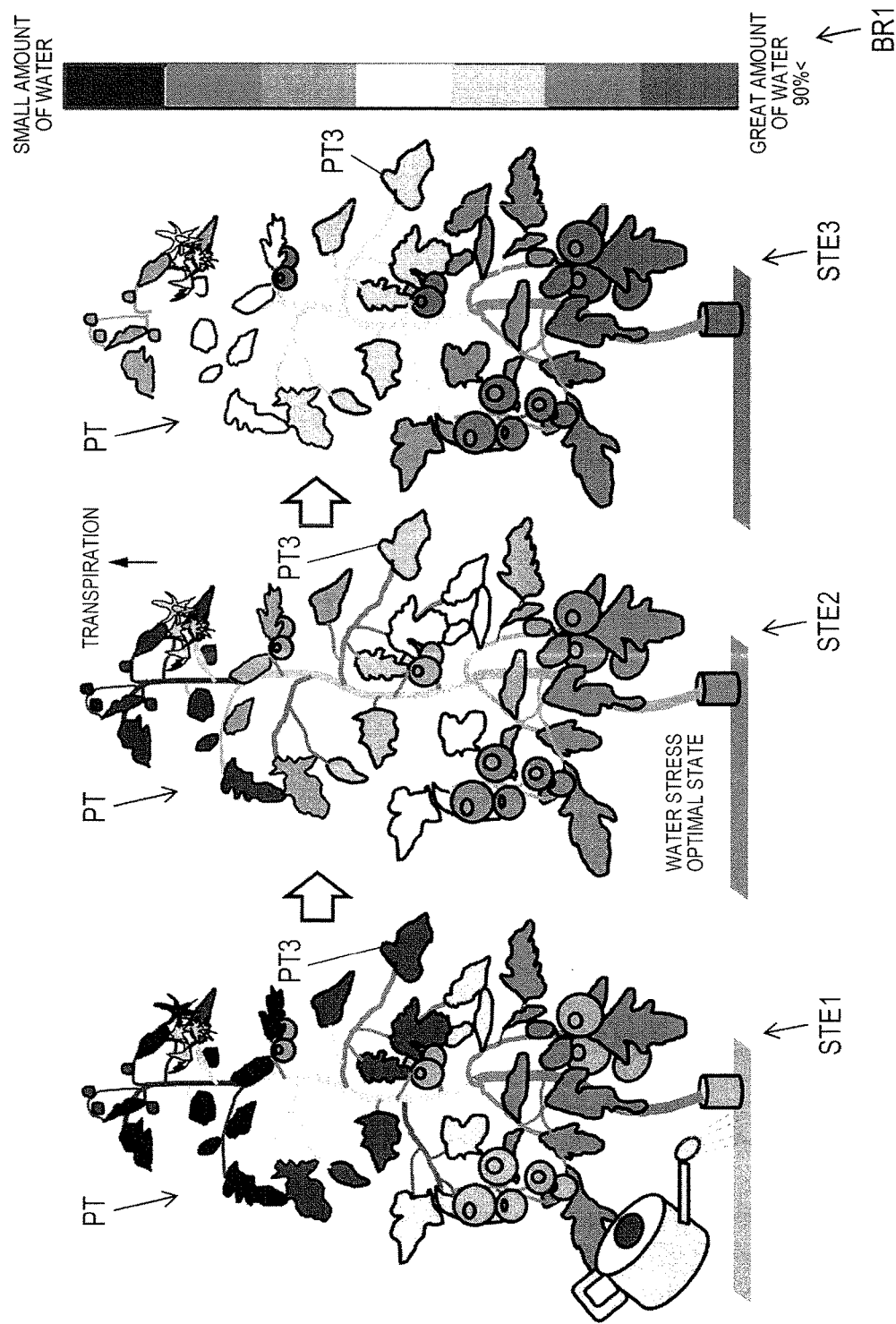
FIG. 12 is an explanatory diagram illustrating an example of a transition of distribution of water of the entirety of the plant in a case where areas of irradiation positions of the reference beam and the measuring beam are the same.

FIG. 12 is an explanatory diagram illustrating an example of a transition of distribution of water of the entirety of plant PT in a case where areas of irradiation positions of reference beam LS1 and measuring LS2 beam are the same. Legend bar BR1 illustrated in FIG. 12 indicates that there is less water the further toward the paper surface upper portion in FIG. 12 and there is more water the further toward the paper surface lower portion in FIG. 12.

State STE1 illustrated in FIG. 12 is a state just before plant PT withers, for example, in a state in which there is no water supplied from fertilizer water supply device WF (for example, water stress state). State STE2 illustrated in FIG. 12 is, for example, a state in which fertilizer or water is supplied from fertilizer or water supply device WF, and a state during absorption of nutrients due to water or fertilizer in roots, stalk PT2, and leaf PT3, and a state in which transpiration is actively performed. State STE3 illustrated in FIG. 12 is, for example, a state after the fertilizer or the water is excessively supplied from fertilizer water supply device WF, and a saturation state in which absorption of nutrients due to the water or the fertilizer in roots, stalk PT2, and leaf PT3 is stopped.

For example, when a distribution state of water of leaf PT3 is described, in state STE1, it is possible to ascertain that water of leaf PT3 is very little, in state STE2, it is possible to ascertain that water of leaf PT3 is slightly insufficient, and in state STE3, it is possible to ascertain that water of leaf PT3 is slightly too much.

In a case where the display data in which the entirety of plant PT that is indicated in step STE1 to step STE3 illustrated in FIG. 12 is included is generated in plant stress detection camera 1 and, for example, is displayed on monitor 50 that is installed within the control room in the office, the user is able to easily ascertain a water absorption rate (in other words, water potential) in plant PT by browsing the display data in which the entirety of plant PT that is indicated in any one of step STE1 to step STE3 is included.

The water potential is a parameter quantitatively indicating how many roots or stalks that potentially draw up water the plant has.

The user is able to easily ascertain the optimal water stress state that is necessary for increasing fruit sugar content and the current water stress state of plant PT in growth of fruit and vegetables such as tomatoes. In FIG. 12, plant PT that is indicated in state STE2 is not necessarily excessively supplied with the fertilizer or the water, and water is not necessarily completely supplied. It is possible for the user to easily ascertain, for example, a state in which water is slightly insufficient in term of water distribution of leaf PT3 and that the state is the optimal water stress state to leaf PT3 by browsing the display data of plant PT that is indicated in step STE2 on monitor 50.

Figure 13:
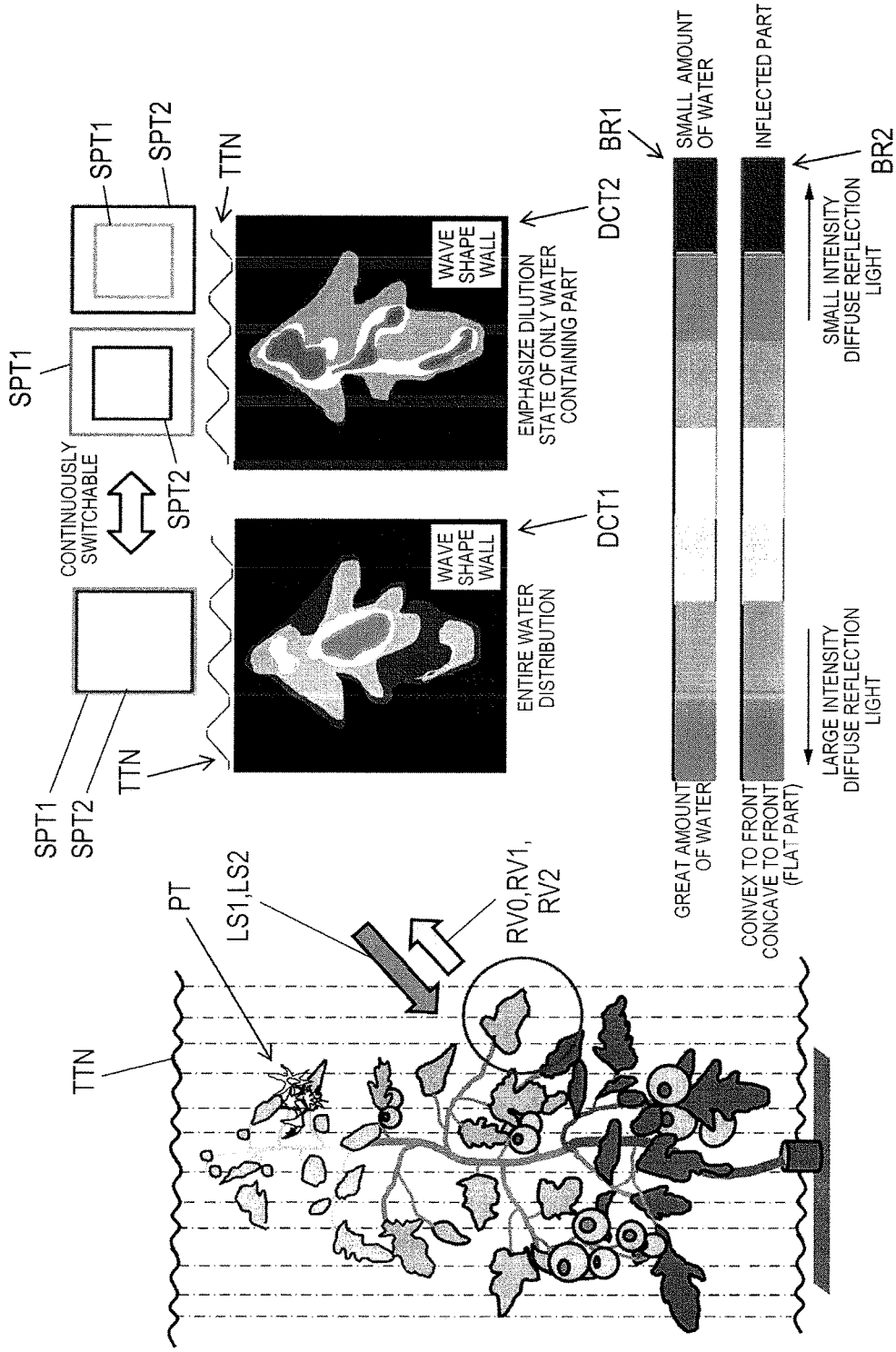
FIG. 13 is an explanatory diagram illustrating an example of a transition of distribution of water or undulation of the leaf of the plant in a case where areas of irradiation positions of the reference beam and the measuring beam are different.
Figure 14:
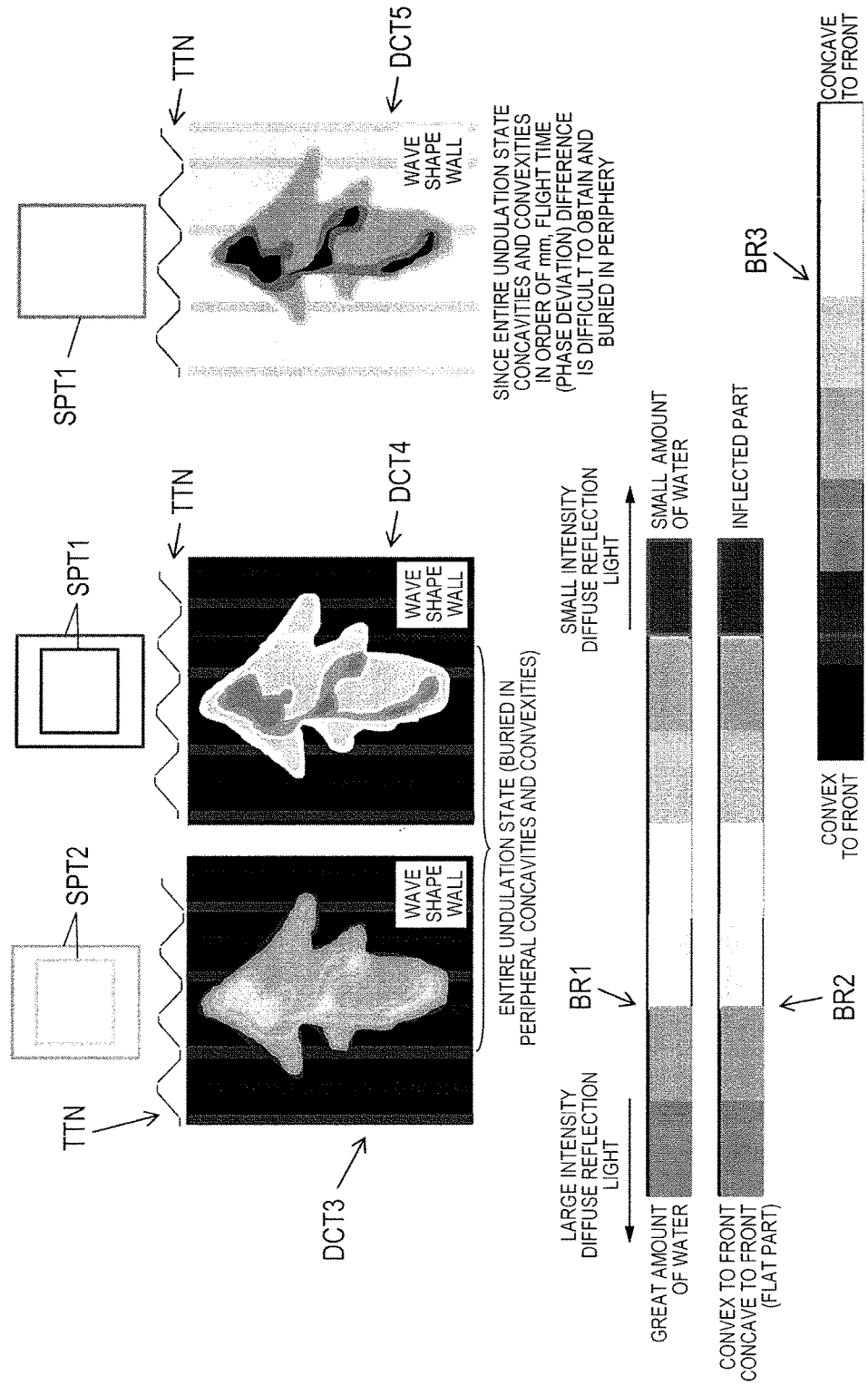
FIG. 14 is an explanatory diagram of a comparative example illustrating an example of a transition of distribution of undulation of the leaf of the plant in a case where areas of irradiation positions are made different using only one out of the reference beam and the measuring beam and a case based on a distance from the plant stress detection camera that is detected using the reference beam.

FIG. 13 is an explanatory diagram illustrating an example of a transition of distribution of water or undulation of leaf PT3 of plant PT in a case where areas of irradiation positions of reference beam LS1 and measuring beam LS2 are different. FIG. 14 is an explanatory diagram of a comparative example illustrating an example of the transition of distribution of undulation of leaf PT3 of plant PT in a case where areas of irradiation positions are different using only one out of reference beam LS1 and measuring beam LS2 and a case based on the distance from plant stress detection camera 1 that is detected using reference beam LS1.

In FIG. 13, for ease of understanding of the description of detection result image data DCT1 and DCT2 of water or undulation, description is made assuming a case in which a wave shape wall TTN made of tin that has undulation in a wave shape in which undulation and concavities and convexities that are apparent in plant PT have the same curvature is provided behind observation target plant PT viewed from plant stress detection camera 1. FIGS. 13 and 14 are described as not detecting water in wave shape wall TTN made of tin.

In legend bars BR1 and BR2 that are indicated in FIGS. 13 and 14, intensity of diffuse reflection light RV1 and RV2 becomes larger toward the paper surface left side in FIGS. 13 and 14 and intensity of diffuse reflection light RV1 and RV2 becomes smaller toward the paper surface right side in FIGS. 13 and 14. In more detail, legend bar BR1 has much water toward the paper surface left side in FIGS. 13 and 14 and has less water toward the paper surface right side in FIGS. 13 and 14. Legend bar BR2 has a shape of the irradiation positions of reference beam LS1 and measuring beam LS2 being more convex to the front or more concave to the front (that is, a flat shape) toward the paper surface left side in FIGS. 13 and 14, and has a shape of the irradiation positions of reference beam LS1 and measuring beam LS2 being more curved (that is, has undulation) toward the paper surface right side in FIGS. 13 and 14.

Detection result image data DCT1 that is indicated in FIG. 13 is detection result image data that is generated by determiner JG of plant stress detection camera 1 in a case where irradiation areas SPT1 and SPT2 of reference beam LS1 and measuring beam LS2 are the same, and indicates a distribution of the detection result which relates to presence or absence of water in the entirety of leaf PT3 of plant PT. Since irradiation areas SPT1 and SPT2 are the same, output which relates to the distribution of undulation of wave shape wall TTN made of tin is not obtained in detection result image data DCT1. According to detection result image data DCT1, the user is able to ascertain that much water is detected in a center part of leaf PT3.

Detection result image data DCT2 that is indicated in FIG. 13 is detection result image data that is generated by determiner JG of plant stress detection camera 1 in a case where irradiation areas SPT1 and SPT2 of reference beam LS1 and measuring beam LS2 are different, and indicates the distribution of the detection result which relates to presence or absence of water and undulation in the entirety of leaf PT3 of plant PT. Since irradiation areas SPT1 and SPT2 are different, weak diffuse reflection light that is reflected on a flat part on the front side and the deep side of wave shape wall TTN made of tin viewed from plant stress detection camera 1 is received in plant stress detection camera 1, respective intensities of diffuse reflection light are indicated in detection result image data DCT2, and are similarly in detection result image data DCT3 and DCT4. However, since the intensity of the diffuse reflection light attenuates more the greater the distance from plant stress detection camera 1, the intensity in the diffuse reflection light that is reflected on the flat part on the depth side viewed from plant stress detection camera 1 is smaller than the intensity of the diffuse reflection light that is reflected on the flat part on the front side.

In detection result image data DCT2 that is indicated in FIG. 13, presence or absence of water is detected in common parts of irradiation areas SPT1 and SPT2, and furthermore, presence or absence of undulation is detected based on a difference between irradiation areas SPT1 and SPT2. Therefore, in detection result image data DCT2, the detection result of undulation is emphasized in only a part in which water is detected in detection result image data DCT1 in comparison to detection result image data DCT1 in which the detection result of undulation is applied to water detection result. Irradiation areas SPT1 and SPT2 may be either large or small. Accordingly, in a case where, for example, both of detection result image data DCT1 and DCT2 that are indicated in FIG. 13 are comparatively displayed on monitor 50, the user is able to simultaneously ascertain change of undulation of opening, curling, or the like of leaf PT3 due to water absorption or transpiration of leaf PT3 that occurs along with change of the amount of water of leaf PT3 by comparatively viewing both detection result image data DCT1 and DCT2.

Detection result image data DCT3 that is indicated in FIG. 14 is detection result image data that is generated by determiner JG of plant stress detection camera 1 in a case where irradiation area SPT2 of only measuring beam LS2 is different in each radiation, and indicates the distribution of the detection result which relates to presence or absence of undulation in the entirety of leaf PT3 of plant PT. Since the wavelength of measuring beam LS2 has a characteristic of tending to be absorbed in water, in detection result image data DCT3, the intensity of diffuse reflection light RV2 is smaller than the intensity of diffuse reflection light RV1 of reference beam LS1, and furthermore, since only one type of measuring beam LS2 is used, it is not possible to accurately discriminate the distribution of undulation of leaf PT3 without a difference from undulation of wave shape wall TTN made of tin that is on the periphery of leaf PT3.

Detection result image data DCT4 that is indicated in FIG. 14 is detection result image data that is generated by determiner JG of plant stress detection camera 1 in a case where irradiation area SPT1 of only reference beam LS1 is different in each radiation, and indicates the distribution of the detection result which relates to presence or absence of undulation in the entirety of leaf PT3 of plant PT. Since the wavelength of reference beam LS1 has a characteristic of tending not to be absorbed in water, in detection result image data DCT4, the intensity of diffuse reflection light RV1 is larger than the intensity of diffuse reflection light RV2 of measuring beam LS2, but since only one type of reference beam LS1 is used, it is not possible to accurately discriminate the distribution of undulation of leaf PT3 although a difference from the intensity of diffuse reflection light is apparent in comparison to undulation of wave shape wall TTN made of tin that is on the periphery of leaf PT3.

Detection result image data DCT5 that is indicated in FIG. 14 is a distance image (TOF image) according to a difference of irradiation time and reception time of diffuse reflection light RV1 in which reference beam LS1 of irradiation area SPT1 is irradiated toward leaf PT3, and indicates the detection result which relates to presence or absence of undulation in the entirety of leaf PT3 of plant PT. In legend bar BR3, a value of the distance from plant stress detection camera 1 becomes larger toward the paper surface left side in FIG. 14 (that is, is convex to the front), and the value of the distance from plant stress detection camera 1 becomes smaller toward the paper surface right side in FIG. 14 (that is, is concave to the front). Since detection result image data DCT5 is generated based on the distance from plant stress detection camera 1, undulation of the shape of the entirety of leaf PT3 is difficult to accurately discriminate.

Figure 15:
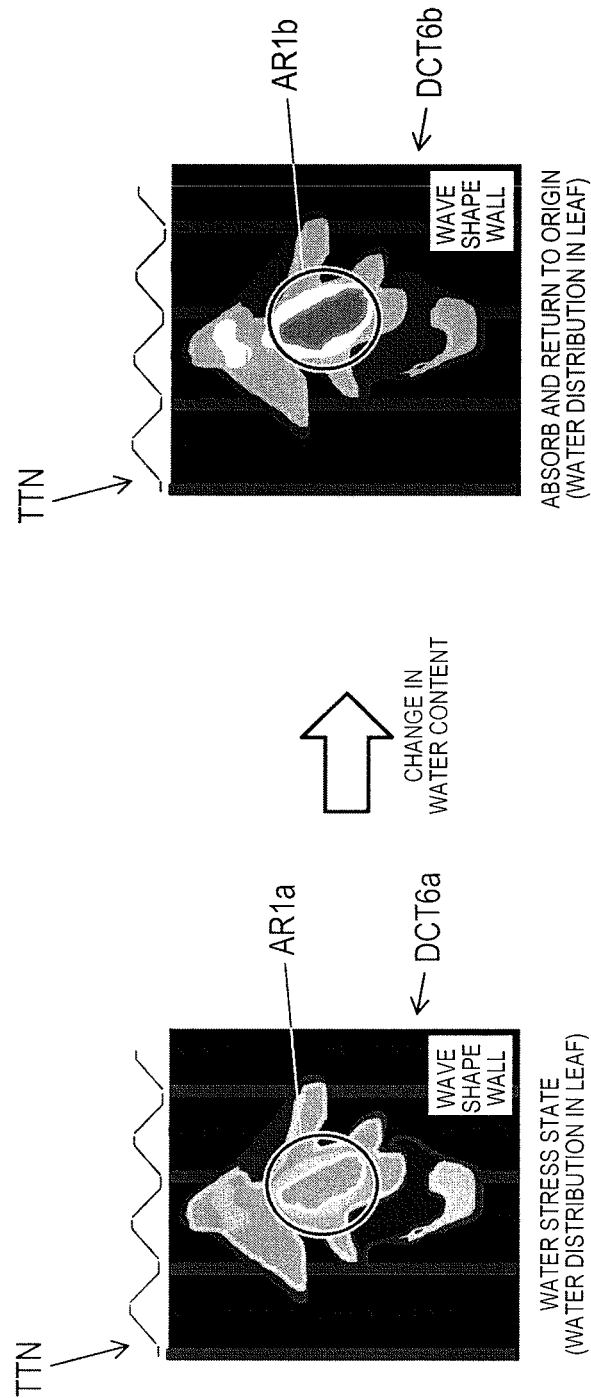
FIG. 15 is an explanatory diagram illustrating an example of the transition of the distribution of water of the leaf of the plant in a case of being changed such that a water content is increased.

FIG. 15 is an explanatory diagram illustrating an example of the transition of the distribution of water of leaf PT3 of plant PT in a case of being changed such that the water content is increased. Also in detection result image data DCT6a and DCT6b that is indicated in FIG. 15, the detection result is indicated in the same manner as the detection result of wave shape wall TTN made of tin that is indicated in FIG. 13 or FIG. 14. Detection result image data DCT6a is detection result image data of water or undulation of leaf PT3 that is in the water stress state. Detection result image data DCT6b is detection result image data of water or undulation of leaf PT3 that is generated after water is supplied.

By supplying the water, since the amount of measuring beam LS2 that is absorbed in water is increased in comparison to prior to water supply, the intensity of diffuse reflection light RV2 is reduced and the intensity ratio (that is, $I_{output905}/I_{output1550}$) of diffuse reflection light RV1 and RV2 is raised. Thereby, in a case where the water content of leaf PT3 is changed so as to rise, the user is able to easily discriminate that a detected amount of water in the entirety of leaf PT3 (for example, range AR1a and range AR1b) is increased by browsing monitor 50 on which detection result image data DCT 6a and 6b is displayed to be comparable.

Figure 16:
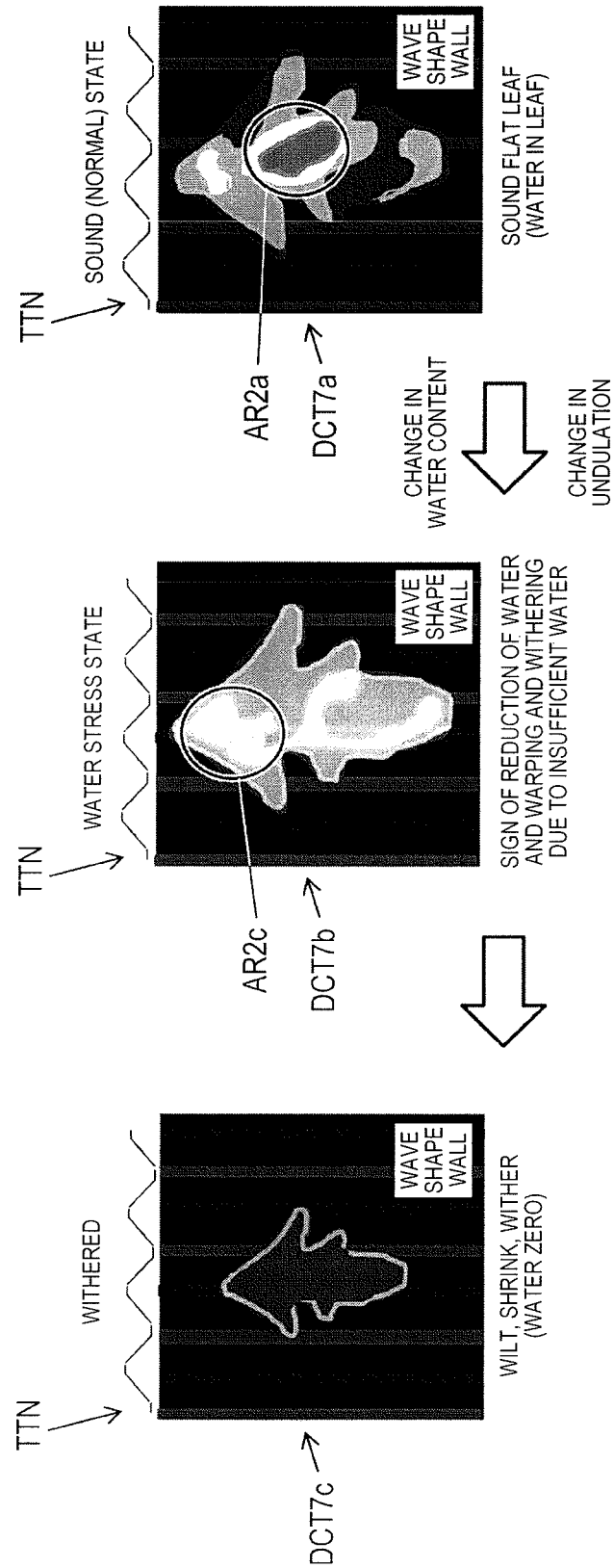
FIG. 16 is an explanatory diagram illustrating an example of the transition of the distribution of water of the leaf of the plant in a case of being changed such that a water content is reduced.

FIG. 16 is an explanatory diagram illustrating an example of the transition of the distribution of water of the leaf of the plant in a case of being changed such that the water content is reduced. Also in detection result image data DCT7a, DCT7b, and DCT7c that are indicated in FIG. 16, the detection result is indicated in the same manner as the detection result of wave shape wall TTN made of tin that is indicated in FIG. 13 or FIG. 14. Detection result image data DCT7a is detection result image data of water or undulation of leaf PT3 that is in a normal sound state (that is, a state in which the water or the fertilizer are supplied at an appropriate amount). Detection result image data DCT7b is detection result image data of water and undulation of leaf PT3 that is in the water stress state, and indicates a sign that water reduces due to shortage of water and the shape of leaf PT3 warps or wilts. Detection result image data DCT7c is detection result image data of water or undulation of leaf PT3 that is generated after water is not supplied, and indicates a withered state in which water is zero.

Due to the water not being supplied, since the amount of measuring beam LS2 that is absorbed in water is reduced, the intensity of diffuse reflection light RV2 is increased and the intensity ratio (that is, $I_{output905}/I_{output1550}$) of diffuse reflection light RV1 and RV2 is reduced. Thereby, in a case where the water content of leaf PT3 is changed so as to reduce, the user is able to easily discriminate that a detected amount of water in the entirety of leaf PT3 (for example, range AR2a, range AR2b, and range AR2c) is reduced by browsing monitor 50 that is displayed to be comparable to detection result image data DCT 7a, 7b, and 7c.

Figure 17B:
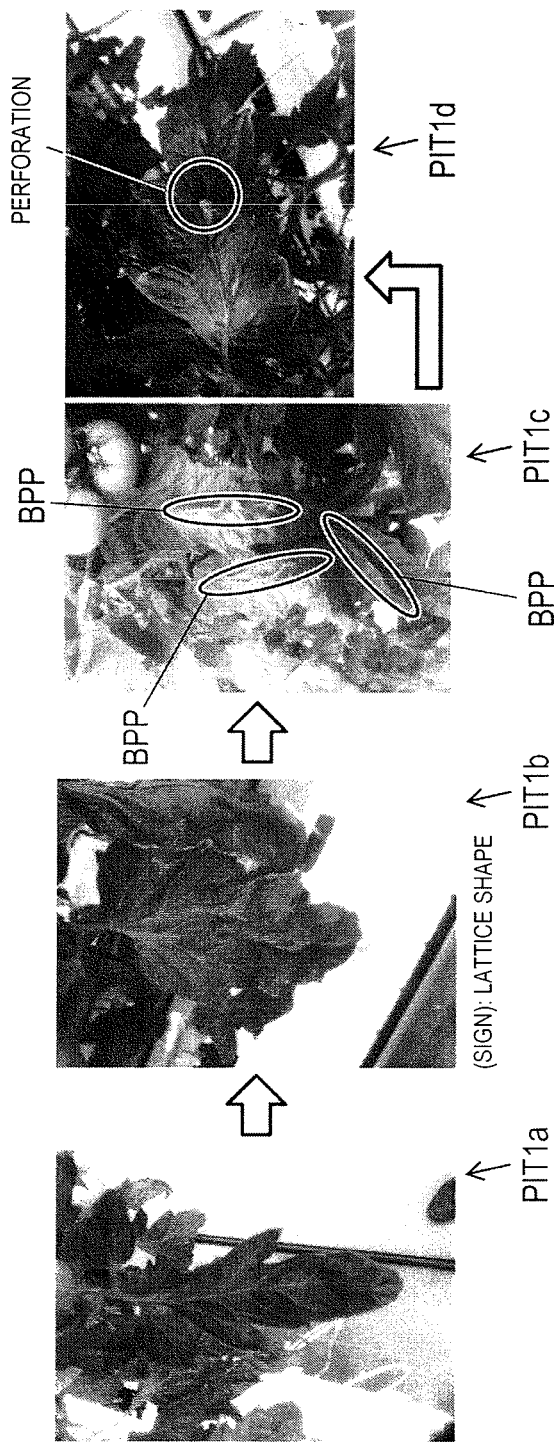
FIG. 17B is a diagram illustrating an example photo of a specific leaf of the transition illustrated in FIG. 17A.

FIG. 17A is a diagram illustrating an example of the transition of the distribution of undulation of the leaf of the plant in a case such that the water content is not changed, but fertilizer that is supplied to the plant is changed to increase. FIG. 17B is a diagram illustrating an example photo of a specific leaf of the transition illustrated in FIG. 17A. Also in detection result image data DCT8a and DCT8b that is indicated in FIG. 17A, the detection result is indicated in the same manner as the detection result of wave shape wall TTN made of tin that is indicated in FIG. 13 or 14. Detection result image data DCT8a is detection result image data of water or undulation of leaf PT3 that is in a normal sound state (that is, a state in which the water or the fertilizer are supplied at an appropriate amount). Detection result image data DCT8b is detection result image data of water and undulation of leaf PT3 that is in a state of overnutrition as a result of fertilizer being excessively supplied and not digested in photosynthesis, and is detection result image data that indicates that undulation is generated by the veins bulging.

There is no change in the water content in detection result image data DCT8a and DCT8b, and the bulging of the veins is caused due to the fertilizer being excessively supplied. Thereby, in a case where the fertilizer is excessively supplied to plant PT, the user is able to easily discriminate that undulation is generated close to range AR3a of leaf PT3 since range AR3a in which it is detected that water is good in, for example, detection result image data DCT8a is shifted to range AR3b in which it is detected that water is good in detection result image data DCT8b by browsing monitor 50 on which detection result image data DCT8a and 8b is displayed to be comparable.

When the fertilizer is excessively supplied as indicated in order of photo PIT1a→photo PIT1b→photo PIT1c→photo PIT1d in FIG. 17B, viewing the sign in which range BPP of three locations of photo PIT1c is a lattice shape in photo PIT1b, it is easy to confirm that range BPP bulges in photo PIT1c, and furthermore, it is easy to confirm that bulging proceeds and a hole is open in the leaf in photo PIT1c.

Figure 18:
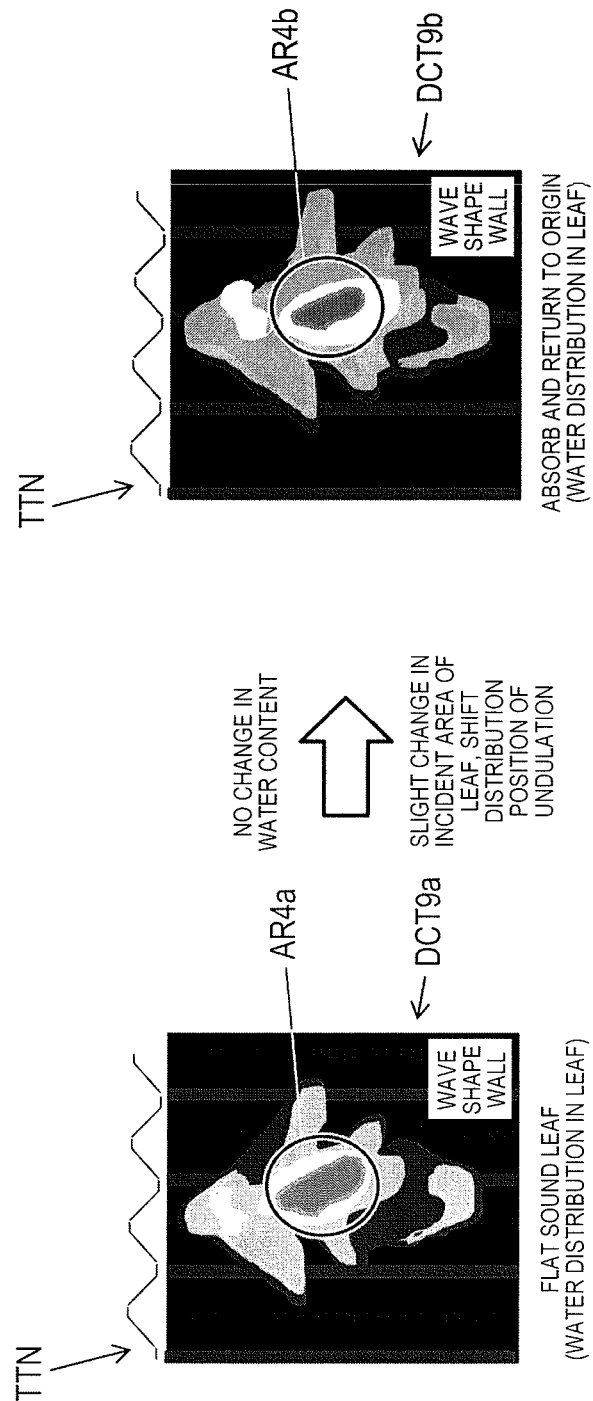
FIG. 18 is an explanatory diagram illustrating an example of the transition of the distribution of undulation of the leaf of the plant in a case where a water content is not changed, but an incident area is changed in the plant stress detection camera of the leaf of the plant.

FIG. 18 is an explanatory diagram illustrating an example of the transition of the distribution of undulation of leaf PT3 of plant PT in a case where the water content is not changed, but an incident area is changed in plant stress detection camera 1 of leaf PT3 of plant PT. Also in detection result image data DCT9a and DCT9b that are indicated in FIG. 18, the detection result is indicated in the same manner as the detection result of wave shape wall TTN made of tin that is indicated in FIG. 13 or 14. Detection result image data DCT9a is detection result image data of the water content or undulation of leaf PT3 that is in a normal sound state (that is, a state in which the water or the fertilizer are supplied at an appropriate amount). Detection result image data DCT9b is detection result image data that is generated in a case where there is no change in water, but the incident area of leaf PT3 of plant stress detection camera 1 is slightly changed due to the influence of blowing of, for example, wind from air conditioning and the like, and indicates that the distribution position of undulation is shifted.

Thereby, in a case where there is no change in the water content, but the incident area of leaf PT3 of plant stress detection camera 1 is slightly changed due to the influence of blowing of, for example, wind from air conditioning and the like, the user is able to easily discriminate that range AR4a in which it is detected that water is good in, for example, detection result image data DCT9a is shifted to range AR4b in which it is detected that water is good in detection result image data DCT9b by browsing monitor 50 on which detection result image data DCT9a and DCT9b is displayed to be comparable.

Figure 19:
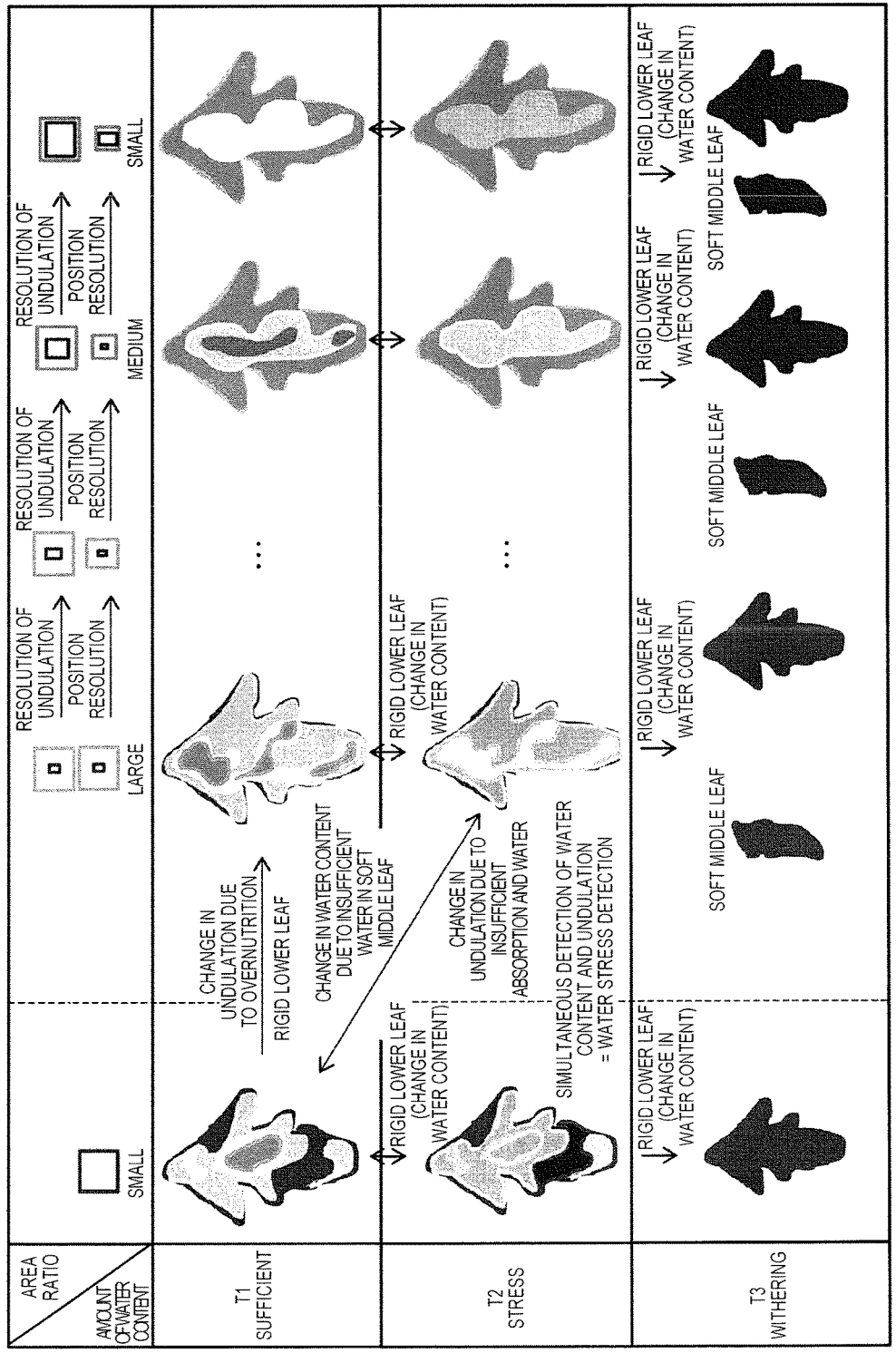
FIG. 19 is a diagram illustrating an example of a correspondence relationship between a detection result of an intensity ratio of the diffuse reflection light and change of water and undulation of the leaf of the plant.

FIG. 19 is a diagram illustrating an example of a correspondence relationship between a detection result of the intensity ratio of the diffuse reflection light and change of water and undulation of leaf PT3 of the plant PT. In a case where the irradiation area of reference beam LS1 and measuring beam LS2 of plant PT are the same, that is, the area ratio is small (refer to the paper surface leftmost end in FIG. 19), it is possible for plant stress detection camera 1 to generate detection result image data in which it is possible to detect the transition of only the distribution of water of leaf PT3. When water stress is high, it is possible to easily discriminate that the amount of detection of water in leaf PT3 is reduced.

In a case where the irradiation area of reference beam LS1 and measuring beam LS2 of plant PT are different, the detection precision of water and undulation deteriorates according to the transition of the area ratio between large, medium, and small. Accordingly, it is concluded that it is desirable to increase the area ratio of reference beam LS1 and measuring beam LS2 that are irradiated from plant stress detection camera 1.

Plant stress detection camera 1 is able to simultaneously detect presence or absence of undulation and not only water in a case where the irradiation areas of reference beam LS1 and measuring beam LS2 of plant PT are easily switched to be set to be the same or set to be different and the irradiation areas of reference beam LS1 and measuring beam LS2 are set to be different.

As described above, plant stress detection camera 1 in the present embodiment radiates reference beam LS1 of the first wavelength (for example, 905 nm) in first beam source 13 by optical scanning toward plant PT, and radiates measuring beam LS2 of the second wavelength (for example, 1550 nm) in second beam source 15 by optical scanning toward plant PT. Plant stress detection camera 1 may be variably set to the irradiation area (first irradiation area) of plant PT on which reference beam LS1 is irradiated and the irradiation area (second irradiation area) of plant PT on which measuring beam LS2 is irradiated, and the first irradiation area and the second irradiation area may not be variably set. In the latter case, the first irradiation area and the second irradiation area are set in advance in plant stress detection camera 1. Plant stress detection camera 1 detects presence or absence of water and undulation of plant PT based on diffuse reflection light RV1 of reference beam LS1 that is reflected on the first irradiation area of set plant PT and diffuse reflection light RV2 of measuring beam LS2 that is reflected on the second irradiation area that is different from the first irradiation area of set plant PT.

Thereby, plant stress detection camera 1 radiates reference beam LS1 of a wavelength that has a characteristic of tending not to be absorbed in water and measuring beam LS2 that has a characteristic of tending to be absorbed in water toward plant PT, and is able to detect at least the distribution state of the presence or absence of water of plant PT with high precision based on the intensity ratio of diffuse reflection light RV1 of reference beam and diffuse reflection light RV2 of measuring beam LS2 that are reflected on the same irradiation position of plant PT. Accordingly, since it is not necessary for an observer of the patent document described above to artificially connect non-polarized electrodes to the plant or soil and it is not necessary for the observer during observation to continue to observe an observation location or close to the observation location, it is possible to reduce complexity of work of the observer.

Plant stress detection camera 1 sets the ratio of the first irradiation area of plant PT on which reference beam LS1 is irradiated and the second irradiation area of plant PT on which measuring beam LS2 is irradiated to m to n (m and n are different values of integers of one or more). In other words, plant stress detection camera 1 sets the first irradiation area of plant PT on which reference beam LS1 is irradiated and the second irradiation area of plant PT2 on which measuring beam LS2 is irradiated to different area ratios. Thereby, plant stress detection camera 1 is able to detect the presence or absence of water with high precision at the irradiation positions of plant PT (for example, leaf PT3) without receiving an influence on presence or absence of undulation of plant PT according to the intensity ratio of diffuse reflection light RV1 of reference beam LS1 and diffuse reflection light RV2 of measuring beam LS2 at the irradiation positions of plant PT (for example, leaf PT3) that is a part of the irradiation area that is common to the first irradiation area and the second irradiation area. When the irradiation areas of plant PT are different, in a case where there is undulation of plant PT in the part of the irradiation area of plant PT, diffuse reflection light in the irradiation area at the width side has a property such that the influence of undulation tends to be received in comparison to the diffuse reflection light in the irradiation area at the narrow side. Utilizing the property, in a case where the first irradiation area and the second irradiation area are different, plant stress detection camera 1 is able to detect presence or absence of undulation with high precision at the irradiation positions of plant PT (for example, leaf PT3) according to the intensity ratio of diffuse reflection light RV1 of reference beam LS1 and diffuse reflection light RV2 of measuring beam LS2 at the irradiation positions of plant PT (for example, leaf PT3).

Plant stress detection camera 1 sets the ratio of the first irradiation area of plant PT on which reference beam LS1 is irradiated and the second irradiation area of plant PT on which measuring beam LS2 is irradiated to one to one. In other words, plant stress detection camera 1 sets the first irradiation area of plant PT on which reference beam LS1 is radiated and the second irradiation area of plant PT2 on which measuring beam LS2 is radiated to be the same. Thereby, plant stress detection camera 1 is able to detect presence or absence of water with high precision at the irradiation positions of plant PT (for example, leaf PT3) without receiving the influence on presence or absence of undulation of plant PT according to the intensity ratio of diffuse reflection light RV1 of reference beam LS1 and diffuse reflection light RV2 of measuring beam LS2 at the irradiation positions of plant PT (for example, leaf PT3) that have the same irradiation areas.

Plant stress detection camera 1 contrasts and displays image data that is obtained by imaging plant PT and the detection result of presence or absence of water of plant PT on monitor 50 that is installed within the control room in the office which is separated from a plastic greenhouse in which plant stress detection camera 1 is disposed. Thereby, plant stress detection camera 1 is able to confirm to the observer whether or not water on observation target plant PT is properly supplied while illuminating the actual image just by the observer looking at monitor 50 that is installed within the control room in the office without being in the plastic greenhouse.

When plant stress detection camera 1 has the zoom operation of the designated location (for example, display location of leaf PT3) of plant PT with respect to monitor 50, the designated location of designated plant PT is enlarged and contrasts and displays image data of the designated location and the detection result of presence or absence of water on monitor 50. Thereby, plant stress detection camera 1 is able to confirm to the observer the distribution state of water of the designated location of plant PT that the observer is to pay particular attention to while illuminating the actual image of the designated location by the easy operation with respect to monitor 50 of the observer.

Plant stress detection camera 1 contrasts and displays image data that is obtained by imaging plant stress detection camera PT and the detection result of presence or absence of water and undulation of plant PT on monitor 50 that is installed within the control room in the office which is separated from a plastic greenhouse in which plant stress detection camera 1 is disposed. Thereby, plant stress detection camera 1 is able to confirm to the observer whether or not water on observation target plant PT is properly supplied, and furthermore, whether or not undulation is generated and bent on observation target plant PT while illuminating the actual image just by the observer looking at monitor 50 that is installed within the control room in the office without being in the plastic greenhouse.

When plant stress detection camera 1 has the zoom operation of the designated location (for example, display location of leaf PT3) of plant PT with respect to monitor 50, the designated location of designated plant PT is enlarged and contrasts and displays image data of the designated location and the detection result of presence or absence of water and undulation on monitor 50. Thereby, plant stress detection camera 1 is able to confirm to the observer the distribution state of water and undulation of the designated location of plant PT that the observer is to pay particular attention to while illuminating the actual image of the designated location by the easy operation with respect to monitor 50 of the observer.

Although the present embodiment is described above while referring to the drawings, needless to say, the present invention is not limited to the examples. According to a person skilled in the art, within the scope which is set forth in the claims, it is obvious that it is possible to conceive of various modified examples and correction examples, and therein is naturally understood as belonging to the technical scope of the present invention.

In the present embodiment described above, description is made using the plant stress detection camera as an example of the plant stress detection apparatus according to the present invention, but the plant stress detection apparatus according to the present invention may be configured such that imaging optics 31, photo detector 33, and image signal processor 35 of visible light camera VSC are omitted. For example, if the plant stress detection apparatus is configured to store in advance one or more set of visible light image data (for example, photo data of observation target plant PT) and include display controller 37 of visible light camera VSC of plant stress detection camera 1 and invisible light sensor NVSS of plant stress detection camera 1, the same effect is obtained as plant stress detection camera 1 of the present embodiment. It is possible to reduce the number of components of the plant stress detection apparatus, and it is possible to suppress manufacturing cost increases of the plant stress detection apparatus. The plant stress detection apparatus may have imaging optics 31, photo detector 33, and image signal processor 35 of visible light camera VSC. Thereby, even if the plant stress detection apparatus stores in advance one or more set of visible light image data (for example, photo data of observation target plant PT), the same effect is obtained as plant stress detection camera 1 of the present embodiment described above.

The detection target distance range described above may be set in a plurality of ranges and not one range. For example, the detection target distance range described above includes 2 to 3 [m] as a first range and 6 to 8 [m] as a second range. In the same manner, the detection target distance range described above may be set to a plurality of values and not one value. In a case where the plurality of detection target distances are input, controller 11 may calculate and set the detection target distance range according to each detection target distance. It is possible to set the detection conditions of plant stress detection camera 1 according to an environment in which plant stress detection camera 1 is installed by being able to set a plurality of detection target distances or detection target distance ranges.

The number of set detection target distances or detection target distance ranges may be arbitrarily increased or reduced. Thereby, it is possible to set the detection conditions of plant stress detection camera 1 according to complexity of the environment in which plant stress detection camera 1 is installed. For example, in a case where the environment is complex (for example, in a case where there are multiple obstacles), the number of detection target distances or detection target distance ranges is set to be great, and in a case where the environment is simple (for example, in a case where there are no obstacles), the number of detection target distances or detection target distance ranges is set to be small.

The plurality of detection target distances or detection target distance ranges may be set in advance, and may be arbitrarily set by the user using data logger DL, communication terminal MT, or the like. Alternatively, the input unit may be provided that is able to be set in plant stress detection camera 1. In the manner of the specific example described above, it is not necessary to set the detection target distance range to both of an upper limit and a lower limit, and either one may be set. For example, the detection target distance range of 100 [m] or more or 5 [m] or less may be set.

In the present embodiment, description may be made in which first beam source 13 is incident in an odd number of incident periods and second beam source 15 is incident in an even number of incident periods, but first beam source 13 and second beam source 15 may be alternately incident in each incident period. For example, first beam source 13 and second beam source 15 may switch the incident timing at different incident periods or random incident periods. In a case where there are a plurality of imaging optics 21 and photo detector 23 (for example, two) in plant stress detection camera 1, reference beam LS1 from first beam source 13 and measuring beam LS2 from second beam source 15 may be simultaneously incident.

In the present embodiment, description is made of plant stress detection camera 1 in which beam output PJ, determiner JG, and visible light camera VSC are integrally configured, but beam output PJ, determiner JG, and visible light camera VSC may be provided separately from each other. For example, beam output PJ and determiner JG may be held in different casings. In the same manner, beam output PJ and visible light camera VSC may be held in different casings. First beam source 13 and second beam source 15 may be provided separately from each other.

However, as in the present embodiment, determiner JG and visible light camera VSC are preferably provided in the same casing. Described in further detail, imaging optics 21 that is utilized in the form of detection result image data and imaging optics 31 that is utilized in the form of visible light image data may be provided in the same casing. It is possible for light receiving positions of two photo detectors to be close by providing imaging optics 21 and 31 in the same casing. That is, it is possible for the detection positions of the detection result image data and the visible light image data to be close. Thereby, it is possible to reduce deviation of the detection result image data and the visible light image data, and it is possible to reduce a load on a synthesis process of the visible light image data and the detection result image data by display controller 37 (for example, pattern matching in step S34, superimposing images in step S35, and the like).

A received signal process may be performed externally to plant stress detection camera 1 (for example, data logger DL or communication terminal MT). For example, the signal process is equivalent to a process of signal processor 25, detection processor 27, display processor 29, image signal processor 35, display controller 37, controller 11, and the like described above. It is possible to reduce the size of plant stress detection camera 1 by providing a function which relates to the signal process externally to plant stress detection camera 1.

The user who browses the display data that is generated by plant stress detection camera 1 of the present embodiment (that is, detection result image data in which the user is able to easily ascertain the water stress state of each seedling of plant PT) on, for example, monitor 50 may operate management PC (refer to the description above) that is installed within the control room in the office and quantitatively measure the water stress state of each seedling of plant PT or the water absorption rate of the roots. In this case, management PC calculates water or the fertilizer amount that are to be given to each seedling using the value of the water stress state or the water absorption rate of the roots that are obtained by measurement, and supply of fertilizer or water is instructed to fertilizer water supply device WF that is indicated in FIG. 1. Plant stress detection camera 1 in the present embodiment is able to be applied to a plant growth observation system that observes growth of each seedling described above.

INDUSTRIAL APPLICABILITY

The present disclosure is utilized as a plant stress detection apparatus and a plant stress detection method which detects a distribution state which relates to at least presence or absence of water stress of a plant with high precision without making work of an observer complex.

REFERENCE MARKS IN THE DRAWINGS 1 plant stress detection camera
11 controller
11a timing controller
13 first beam source
15 second beam source
17 beam scanner
21, 31 imaging optics
23, 33 photo detector
25 signal processor
25a I/V converter 25b amplifier circuit
25c comparator/peak hold
27 detection processor
27a distance/water and undulation detector
27b memory
27c detection result filter
29 display processor
35 image signal processor
37 display controller
JG determiner
LS1 reference beam
LS2 measuring beam
MT communication terminal
NVSS invisible light sensor
PJ beam output
TR timing signal for beam scanning
RF beam output signal
RV0 ambient light
RV1, RV2 diffuse reflection light
VSC visible light camera

The invention claimed is:

1. A plant stress detection apparatus, comprising:
a first light source that radiates a reference beam of a first wavelength that has a characteristic of tending not to be absorbed in water toward a plant by optical scanning;
a second light source that radiates a measuring beam of a second wavelength that has a characteristic of tending to be absorbed in water toward the plant by optical scanning; and
a sensor that detects a presence or an absence of water and an undulation of the plant based on reflection light of the reference beam that is reflected at an irradiation position of the plant that has a first irradiation area and reflection light of the measuring beam that is reflected at an irradiation position of the plant that has a second irradiation area that is different from the first irradiation area.

2. The plant stress detection apparatus of claim 1, further comprising:
a controller that sets the first irradiation area and the second irradiation area to vary.

3. The plant stress detection apparatus of claim 2,
wherein the controller sets a ratio of the first irradiation area to the second irradiation area as 1:1.

4. The plant stress detection apparatus of claim 3, further comprising:
a camera that images the plant; and
a display controller that displays image data of the plant that is imaged by the camera on a display, the image data displaying a detection result of the presence or the absence of the water of the plant that is detected by the sensor.

5. The plant stress detection apparatus of claim 4,
wherein the display controller enlarges a designated location of the plant, with respect to the display, according to a zoom operation of the designated location of the plant, compares image data of the designated location and the detection result of the presence or the absence of the water, and displays the designated location and a comparison result on the display.

6. The plant stress detection apparatus of claim 1, further comprising:
a camera that images the plant; and
a display controller that displays image data of the plant that is imaged by the camera on a display, the image data displaying a detection result of the presence or the absence of the water and the undulation of the plant that are detected by the sensor.

7. The plant stress detection apparatus of claim 6,
wherein the display controller enlarges a designated location of the plant, with respect to the display, according to a zoom operation of the designated location of the plant, compares image data of the designated location and the detection result of the presence or the absence of the water and the undulation, and displays the designated location and a comparison result on the display.

8. A plant stress detection method for a plant stress detection apparatus, the plant stress detection method comprising:
radiating a reference beam of a first wavelength that has a characteristic of tending not to be absorbed in water toward a plant by optical scanning;
radiating a measuring beam of a second wavelength that has a characteristic of tending to be absorbed in water toward the plant by optical scanning; and
detecting a presence or an absence of water and an undulation of the plant based on reflection light of the reference beam that is reflected at an irradiation position of the plant that has a first irradiation area and reflection light of the measuring beam that is reflected at an irradiation position of the plant that has a second irradiation area that is different from the first irradiation area.

9. The plant stress detection apparatus of claim 2,
wherein the controller is a processor.

10. The plant stress detection apparatus of claim 1,
wherein the sensor is a photo detector.

* * * * *